US012311060B2

(12) United States Patent
Collins et al.

(10) Patent No.: US 12,311,060 B2
(45) Date of Patent: *May 27, 2025

(54) MODIFIED RELEASE PHARMACEUTICAL COMPOSITIONS OF HUPERZINE AND METHODS OF USING THE SAME

(71) Applicant: Biscayne Neurotherapeutics, Inc., Rockville, MD (US)

(72) Inventors: Stephen D. Collins, Lake Forest, IL (US); Peter Goldstein, Hollywood, FL (US); Joshua T. Johnstone, Apex, NC (US)

(73) Assignee: Biscayne Neurotherapeutics, Inc., Rockville, MD (US)

( * ) Notice: Subject to any disclaimer, the term of this patent is extended or adjusted under 35 U.S.C. 154(b) by 261 days.

This patent is subject to a terminal disclaimer.

(21) Appl. No.: 17/387,329

(22) Filed: Jul. 28, 2021

(65) Prior Publication Data

US 2021/0353552 A1 Nov. 18, 2021

Related U.S. Application Data

(62) Division of application No. 15/985,390, filed on May 21, 2018, now abandoned.

(60) Provisional application No. 62/508,554, filed on May 19, 2017.

(51) Int. Cl.
| | | |
|---|---|---|
| A61K 9/50 | (2006.01) | |
| A61K 9/48 | (2006.01) | |
| A61K 31/435 | (2006.01) | |
| A61K 47/32 | (2006.01) | |
| A61K 47/38 | (2006.01) | |
| A61P 25/08 | (2006.01) | |

(52) U.S. Cl.
CPC ............. *A61K 9/5078* (2013.01); *A61K 9/48* (2013.01); *A61K 9/5042* (2013.01); *A61K 31/435* (2013.01); *A61K 47/32* (2013.01); *A61K 47/38* (2013.01); *A61P 25/08* (2018.01)

(58) Field of Classification Search
CPC ..... A61P 25/08; A61K 9/5078; A61K 9/5042; A61K 47/32; A61K 47/38; A61K 31/435; A61K 9/48
See application file for complete search history.

(56) References Cited

U.S. PATENT DOCUMENTS

| | | | |
|---|---|---|---|
| 5,009,895 A | 4/1991 | Lui | |
| 8,193,212 B2 | 6/2012 | Schachter | |
| 11,351,120 B2* | 6/2022 | Collins | A61K 9/5078 |
| 2006/0045865 A1 | 3/2006 | Jacob et al. | |
| 2007/0065512 A1* | 3/2007 | Dedhiya | A61K 9/5078 |
| | | | 514/662 |
| 2011/0224245 A1 | 9/2011 | Schachter | |
| 2013/0040982 A1* | 2/2013 | Friedman | A61P 25/28 |
| | | | 514/295 |
| 2015/0335624 A1 | 11/2015 | Collins et al. | |
| 2016/0136103 A1 | 5/2016 | Boudy et al. | |
| 2016/0206602 A1 | 7/2016 | Reynolds | |
| 2023/0090653 A1* | 3/2023 | Collins | A61K 9/5042 |

FOREIGN PATENT DOCUMENTS

| | | |
|---|---|---|
| CN | 1208054 C | 6/2005 |
| CN | 1751683 A | 3/2006 |
| CN | 101081217 A | 12/2007 |
| CN | 1682719 B | 4/2010 |
| CN | 101732312 A | 6/2010 |
| CN | 1726911 B | 8/2010 |
| CN | 101264058 B | 9/2010 |
| CN | 101485640 B | 3/2011 |
| CN | 101987081 A | 3/2011 |
| CN | 101485639 B | 4/2011 |
| CN | 102834095 A | 12/2012 |
| CN | 102512395 B | 10/2013 |
| CN | 103417505 A | 12/2013 |
| CN | 103687849 A | 3/2014 |
| ES | 2351709 T3 | 2/2011 |
| JP | H07-053364 A | 2/1995 |
| JP | 2002-533396 A | 10/2002 |
| JP | 2010-526054 A | 7/2010 |
| JP | 2010-275314 A | 12/2010 |
| JP | 2013-536186 A | 9/2013 |
| JP | 2014-521713 A | 8/2014 |
| JP | 2017-031189 A | 2/2017 |
| WO | WO-00/38686 A1 | 7/2000 |
| WO | WO-0132115 A1 * | 5/2001 ............. A61K 31/44 |

(Continued)

OTHER PUBLICATIONS

Howard C Ansel, et al, New Drug Development and Approval Process in Pharmaceutical Dosage Forms and Drug Delivery Systems Seventh Edition, 48-51, Lippincott Williams & Wilkins (Year: 1999).*

Maung Kyaw Moe Tun & Seth B Herzon, The Pharmacology and Therapeutic Potential of (-)-Huperzine A, 4 J Exp. Pharmacol. 113 (Year: 2012).*

J.C. Ye, et al, Pharmacokinetics of Huperzine A after Transdermal and Oral Administration in Beagle Dogs, 356 Int'l J Pharmaceut. 187 (Year: 2008).*

(Continued)

*Primary Examiner* — Sean M Basquill

(74) *Attorney, Agent, or Firm* — Foley & Lardner LLP

(57) ABSTRACT

The present application discloses pharmaceutical compositions for modified release of huperzine. The pharmaceutical compositions and methods described herein, allow for dosing of huperzine at higher therapeutic thresholds, while avoiding rapid serum peak plasma levels, thereby avoiding the adverse nausea and vomiting associated with the immediate release pharmaceutical compositions. Methods of treating neurological disorders and/or seizure disorders with the modified release compositions is also described.

34 Claims, 9 Drawing Sheets

(56) References Cited

FOREIGN PATENT DOCUMENTS

| WO | WO-2004/030633 A2 | 4/2004 |
|---|---|---|
| WO | WO-2004/037190 A2 | 5/2004 |
| WO | WO-2008/132712 A2 | 11/2008 |
| WO | WO-2011/054759 A1 | 5/2011 |
| WO | WO-2011/095973 A1 | 8/2011 |
| WO | WO-2012/006959 A1 | 1/2012 |
| WO | WO-2012/006961 A1 | 1/2012 |
| WO | WO-2012/019990 A2 | 2/2012 |
| WO | WO-2012/121863 A1 | 9/2012 |
| WO | WO-2012/129759 A1 | 10/2012 |
| WO | WO-2013/024023 A1 | 2/2013 |
| WO | WO-2013/139195 A1 | 9/2013 |
| WO | WO-2014/107685 A2 | 7/2014 |

OTHER PUBLICATIONS

Ha, et al, Huperzine A as Potential Treatment of Alzheimer's Disease: An Assessment on Chemistry, Pharmacology, and Clinical Studies, 8 Chem. Biodiver. 1189 (Year: 2011).*
Jennifer Dressman, Comparison of Canine and Human Gastrointestinal Physiology, 3 Pharma. Res. 123 (Year: 1986).*
P. Zane, et al, Use of the Pentagastrin Dog Model to Explore the Food Effects on Formulations in Early Drug Development, 57 Eur. J Pharma. Sci. 207 (Year: 2014).*
Biscayne Neurotherapeutics Reports Successful Phase 1b Clinical Trial Results for Its Novel Antiepileptic Agent, Oct. 19, 2017, 3 pages.
Chu et al., "Pharmacokinetics Of Huperzine A In Dogs Following Single Intravenous And Oral Administrations," Planta Med, 2006, 72(6):552-555.
Drugs & Therapy Bulletin, "Standardized dosing times," Nov./Dec. 2007, 21(10):1-3.
English translation of Chinese Patent Application No. 101081217 A, "Slow-release small pill preparation containing huperzine A and method for making same", (filed May 30, 2006; published Dec. 5, 2007; previously cited on Sep. 4, 2018).
English translation of Chinese Patent Application No. 101264058 B, "Huperzine A and its derivative or salts sustained-release nanometer granule and preparing method thereof", (filed Mar. 13, 2007; published Sep. 1, 2010; issued Sep. 1, 2010; previously cited on Sep. 4, 2018).
English translation of Chinese Patent Application No. 101485640 B, "Huperzine A mono-layer osmotic pump controlled release tablets", (filed Jan. 18, 2008; published Mar. 23, 2011; previously cited on Sep. 4, 2018).
English translation of Chinese Patent Application No. 102512395 B, "Huperzine osmotic-pump controlled release tablet", (filed Dec. 30, 2011; published Oct. 9, 2013; issued Oct. 9, 2013; previously cited on Sep. 4, 2018).
English translation of Chinese Patent Application No. 1208054 C, "Use of huperzine for neuropathic pain", (Schachter, S.C.; filed May 23, 2006; published Nov. 23, 2006; issued Jun. 5, 2012; previously cited on Sep. 4, 2018).
English translation of Chinese Patent Application No. 1682719 B, "Enteric soluble coating slow releasing tablet containing huperzine A and preparing method", (filed Mar. 1, 2005, published Apr. 28, 2010; issued Apr. 28, 2010; previously cited on Sep. 4, 2018).
Gao et al., "Controlled release of huperzine A from biodegradable microspheres: In vitro and in vivo studies," International Journal of Pharmaceutics, 2007, 330:1-5.
International Search Report in PCT PCT/US2018/033722 dated Sep. 20, 2018.
Liu et al., "Preparation and in vitro and in vivo release studies of Huperzine A loaded microspheres for the treatment of Alzheimer's disease," Journal of Controlled Release, 2005, 107:417-427.
Machine English translation of CN 101081217, 2007.
Surelease product information (year: 2016).
Surelease Application Data, Corolcon, 2011, 1-5.
Damar et al., "Huperzine A: A promising anticonvulsant, disease modifying, and memory enhancing treatment option in Alzheimer's disease," Medical Hypotheses, Feb. 2017, 99:57-62.
Peng et al., "Huperzine A loaded multiparticulate disintegrating tablet: Drug release mechanism of ethyl cellulose microparticles and pharmacokinetic study," Powder Technology—Electrostatic Phenomena in Particulate Processes, Jul. 19, 2019, 355:649-656.

* cited by examiner

MODIFIED RELEASE PHARMACEUTICAL COMPOSITIONS OF HUPERZINE AND METHODS OF USING THE SAME

CROSS-REFERENCE TO RELATED APPLICATIONS

The present application is a Continuation of U.S. application Ser. No. 15/985,390, filed May 21, 2018, which claims benefit of and priority to U.S. Provisional No. 62/508,554 entitled "EXTENDED RELEASE FORMULATIONS OF HUPERZINE AND METHODS OF USING THE SAME," filed May 19, 2017, the contents of which is hereby incorporated by reference in its entirety.

SUMMARY OF THE INVENTION

Huperzine A is a naturally occurring sesquiterpene alkaloid compound found in the firmoss *Huperzia serrata*. It is a potent inhibitor of acetylcholinesterase. In several countries, Huperzine A is sold as a dietary supplement for memory support. In China, huperzine A is State Food and Drug Administration (SFDA) approved for the treatment of dementia.

Huperzine A has been administered to healthy volunteers and patients in numerous trials, many in China, demonstrating acceptable safety and tolerability as well as efficacy in Alzheimer's disease, benign senescent forgetfulness, vascular dementia, myasthenia gravis, schizophrenia, and cocaine dependence. The dosages used in these trials were between 0.01 and 0.8 mg/day via oral administration or intramuscular injection. While these studies showed a favorable safety profile, in some studies, transient dose related nausea occurred at the higher dose levels.

Applicants conducted a dose escalation study in patients with drug-resistant epilepsy, to investigate the safety and tolerability of immediate release pharmaceutical compositions of huperzine A. In this study, patients experienced serious adverse events (nausea and vomiting), many within the first 31 hours, most probably due to the rapid serum exposure of the immediate release pharmaceutical composition. (vide infra).

There are no available published data on the efficacy of huperzine A in patients with epilepsy in the medical or patent literature. Nonclinical data in rodent models show that huperzine A has very high efficacy as an anticonvulsant, with mechanisms of action that are markedly different from available anti-epileptic drugs (AEDs). Applicants however, have predicted that higher doses of huperzine than previously administered in clinical trials, will be needed to achieve efficacy in treating seizure disorders in patients (vide infra).

While huperzine A could potentially provide additional beneficial effects in the areas of neurological disorders, seizure disorders, memory and language impairment, immediate release pharmaceutical compositions of huperzine A are inadequate for treating disorders where higher therapeutic thresholds are needed due to dose-related adverse events, especially in patients with chronic conditions. Immediate release pharmaceutical compositions also have the added drawback of requiring dosing 4 to 6 times daily due to the fast $t_{1/2}$ associated with these pharmaceutical compositions. Dosing 4 to 6 times daily is unacceptable in many patient populations, for example, those related to memory loss or seizures, as compliance becomes a major issue for these patients. Nonclinical studies suggest that higher doses than those used previously, such as up to 5 mg/day, may be safe if delivered with a pharmaceutical composition that reduces high peak-trough serum levels.

A slow release pill containing Huperzine A has been reported by Zhou et al. in Chinese patent application CN101081217, however, these pharmaceutical compositions fail to significantly reduce peak plasma concentrations compared with immediate release pharmaceutical compositions and also fail to extend the $t_{max}$. As a result, these pharmaceutical compositions would not overcome the serious adverse events associated with rapid, high peak serum concentrations and would require dosing 4-6 times a day, thus offering no advantage over immediate release pharmaceutical compositions.

The present invention allows for the plasma exposure necessary for achieving efficacy while maintaining a desirable safety profile not attainable with previously known pharmaceutical compositions of huperzine.

Embodiments of the present invention relate to pharmaceutical compositions for oral delivery of huperzine that may be used to treat various neurological disorders and diseases, for example, pain, Alzheimer's disease, and seizure disorders. The modified release pharmaceutical compositions of huperzine described herein, allow for optimal efficacy of huperzine with either reduced duration, severity and/or risk of the serious adverse events associated with immediate release pharmaceutical compositions that are either dose limiting or completely prevent the continued use of huperzine.

Embodiments of the invention are directed to a pharmaceutical composition for oral delivery comprising: (a) about 74 to 86 weight % of a sugar sphere core wherein the sugar sphere core has a particle size of about 500-710 µm; (b) a huperzine layer coating the sugar sphere, wherein the huperzine layer comprises about 0.95 weight % to about 1 weight % huperzine or a pharmaceutically acceptable salt of huperzine that is equivalent to about 0.95 weight % to about 1 weight % huperzine, and one or more excipients, wherein the total amount of excipients is about 5 weight % to about 9 weight %; and (c) about 7 weight % to 16 weight % of an plasticized ethyl cellulose polymer layer coating the huperzine layer, wherein the huperzine layer comprises a therapeutically-effective amount of huperzine. In some embodiments the huperzine is huperzine A or a pharmaceutically acceptable salt thereof.

Some embodiments of the invention are directed to a pharmaceutical composition comprising: (a) about 80 weight % to about 83 weight % of a sugar sphere core wherein the sugar sphere core has a particle size of about 500-710 µm; (b) a huperzine layer coating the sugar sphere, wherein the huperzine layer comprises about 0.95 weight % to about 1 weight % huperzine A or a pharmaceutically acceptable salt of huperzine A that is equivalent to about 0.95 weight % to about 1 weight % huperzine A, about 5 weight % to about 6 weight % hydroxypropyl methylcellulose, and about 0.95 weight % to about 1 weight % polyvinylpyrrolidone; and (c) about 8 weight % to about 12 weight % of a plasticized ethyl cellulose polymer layer coating the huperzine layer, wherein the huperzine layer comprises a therapeutically-effective amount of huperzine A.

Some embodiments of the present inventions are directed to a pharmaceutical composition characterized by a $C_{max}$ of huperzine A in plasma of about 4 ng/mL to about 8 ng/mL, a $T_{max}$ of about 4 hours to about 8 hours and a $t_{1/2}$ of about 8 hours to about 12 hours, upon oral administration of a therapeutically effective dose of the composition to a human subject. In one embodiment the $C_{max}$ is about 4 ng/mL to about 6 ng/mL, $T_{max}$ is about 4 hours to about 8 hours and the $t_{1/2}$ is about 10 hours to about 12 hours. In one embodiment the $C_{max}$ is about 6 ng/mL, the $T_{max}$ is about 4 hours and the $t_{1/2}$ is about 8.3 hours.

Some embodiments of the invention are to a pharmaceutical composition comprising a therapeutically-effective amount of huperzine A, characterized by a $T_{max}$ of about 4 hours to about 8 hours and a $C_{max}$ that is reduced by about 25% to about 75% when compared with a $C_{max}$ of an immediate release huperzine pharmaceutical composition administered at an equivalent dose. In some embodiments the $C_{max}$ is reduced by 50% when compared with a $C_{max}$ of an immediate release huperzine pharmaceutical composition administered at an equivalent dose.

Some embodiments of the present invention are directed to a pharmaceutical composition that exhibits the following dissolution profile when tested according to USP 1 type apparatus at 50 revolutions per minute in 50 mM phosphate (pH 6.8) at 37° C.: about 36% to about 46% of the huperzine is released after 2 hours, about 61% to about 77% of the huperzine is released after 4 hours, about 84% to about 97% of the huperzine is released after 8 hours and not less than about 89% of the huperzine is released after 12 hours.

Some embodiment of the invention describe a method of treating a neurological disorder and/or seizure disorders comprising administering a pharmaceutical composition according to any embodiment described herein. In some embodiments, the composition is administered once daily or twice daily. In some embodiments, the composition is administered for at least 1 day, at least 2 days, at least 3 days, at least 4 days, at least 5 days, at least 6 days, at least 7 days, at least 8 days, at least 9 days, at least 10 day, at least 11 days, at least 12 days, at least 13 days, at least 14 days, at least 1 month, at least 2 months, at least 3 months, at least 4 months, at least 5 months, at least 6 months or for so long as the subject is in need of treatment. In some embodiments, the composition is administered in a titration regimen, wherein the dose of huperzine is increased in increments of 0.25 mg or 0.5 mg every two days or up to two weeks. In some embodiments the seizure disorder is epilepsy or complex partial seizures.

Some embodiment of the invention describe a method of treating a disorder selected from the group consisting of a neurological disorder and a seizure disorder, in a patient in need thereof, wherein the patient experiences a better side effect profile, comprising administering one or more titration doses of huperzine A, followed by administering a maintenance dose of huperzine A; wherein the huperzine A is administered in a modified release pharmaceutical 1 composition of huperzine A. In some embodiments the modified release pharmaceutical is a modified release pharmaceutical according to any embodiment described herein.

Some embodiments of the invention describe a method of treating a neurological disorder and/or a seizure disorder, in a patient in need thereof, wherein the patient experiences a better side effect profile, comprising administering a first dosing regimen of at least one dosing regimen selected from a. to h. (as further described below) and administering a second dosing regimen of at least one dosing regimen selected from a. to i. (as further described below), provided the second dosing regimen ascends from the first dosing regimen and further provided the last dosing regimen is the maintenance dose and therefore will be administered for as long as the patient is in need of treatment thereof:

a. administering a dose of about 0.25 mg of huperzine A, once every about 12 hours for at least two days and up to two weeks;

b. administering a dose of about 0.5 mg of huperzine A, once every about 12 hours for at least two days and up to two weeks;

c. administering a dose of about 0.75 mg of huperzine A, once every about 12 hours for at least two days and up to two weeks;

d. administering a dose of about 1 mg of huperzine A, once every about 12 hours for at least two days and up to two weeks;

e. administering a dose of about 1.25 mg of huperzine A, once every about 12 hours for at least two days and up to two weeks;

f. administering a dose of about 1.5 mg of huperzine A, once every about 12 hours for at least two days and up to two weeks;

g. administering a dose of about 1.75 mg of huperzine A, once every about 12 hours for at least two days and up to two weeks;

h. administering a dose of about 2 mg of huperzine A, once every about 12 hours for at least two days and up to two weeks;

i. administering a dose of about 2.5 mg of huperzine A, once every about 12 hours for at least two days;

wherein the huperzine A of a.-i. is administered in a modified release pharmaceutical composition of huperzine A. In some embodiments the modified release pharmaceutical composition is a pharmaceutical composition according to any embodiment described herein.

Some embodiments describe a method of treating a disorder selected from the group consisting of a neurological disorder and/or a seizure disorder, to a patient in need thereof, wherein the patient experiences a better side effect profile, comprising administering a modified release pharmaceutical composition of huperzine A, wherein the modified release pharmaceutical composition of huperzine A is characterized by a $C_{ss}$ of huperzine A in plasma selected from the group consisting of: about 0.52 to about 0.82 ng/mL at a 0.25 mg dose; about 1.91 to about 2.99 ng/mL at a 0.50 mg dose; about 3.56 to about 5.55 ng/mL at a 0.75 mg dose; about 5.58 to about 8.72 ng/mL at a 1 mg dose; about 8.22 to about 12.84 ng/mL at a 1.25 mg dose; about 9.02 to about 14.09 ng/mL at a 1.5 mg dose; about 10.04 to about 15.69 ng/mL at a 1.75 mg dose; about 16 to about 25 ng/mL at a 2.0 mg dose; and about 18.48 to about 28.88 ng/mL at a 2.5 mg dose. In some embodiments, the modified release pharmaceutical composition is according to any embodiment described herein.

Some embodiments describe a method of treating a disorder selected from the group consisting of a neurological disorder and/or a seizure disorder, in a patient in need thereof, wherein the patient experiences a better side effect profile, comprising administering a modified release pharmaceutical composition of huperzine A, wherein the modified release pharmaceutical composition of huperzine A is characterized by a $C_{ss}$ of huperzine A in plasma of at least 8 ng/mL when administered at a therapeutically effective dose Some embodiments describe a method of treating a disorder selected from the group consisting of a neurological disorder and a seizure disorder, to a patient in need thereof, wherein the patient experiences a better side effect profile, comprising administering a modified release pharmaceutical composition of huperzine A, wherein the modified release pharmaceutical composition of huperzine A is characterized by a $C_{max}$ of huperzine in plasma of about 0.76 ng/mL to about 1.19 ng/mL, a $T_{max}$ of about 4 hour to about 6.25 hours and an $AUC_{0-8}$ of about 4.18 µg·h/L to about 6.53 µg·h/L upon oral administration of a therapeutically effective dose of the pharmaceutical composition to a human subject.

Some embodiments describe a method of treating a disorder selected from the group consisting of a neurological disorder and a seizure disorder, to a patient in need thereof, wherein the patient experiences a better side effect profile, comprising administering a modified release pharmaceutical composition of huperzine A, wherein the modified release pharmaceutical composition of huperzine A is characterized by a $C_{max}$ of huperzine in plasma of about 2.51 ng/mL to about 3.93 ng/mL, a $T_{max}$ of about 4 hour to about 6.25 hours and an $AUC_{0-8}$ of about 13.76 to about 21.5 upon oral administration of a therapeutically effective dose of the pharmaceutical composition to a human subject.

DETAILED DESCRIPTION

Definitions

Figure 1:
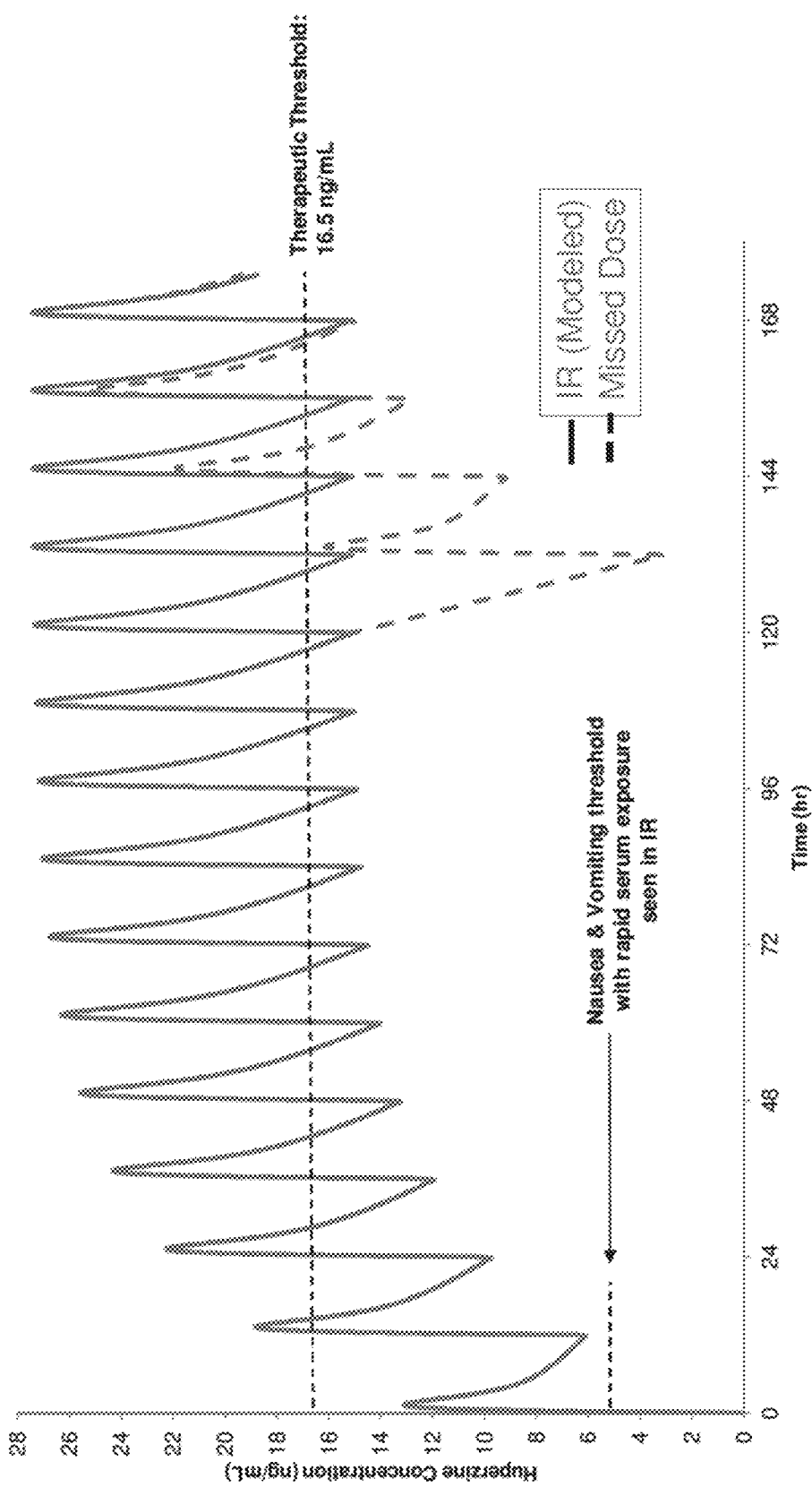
FIG. 1 shows the modeled plasma levels of huperzine A following immediate release dosing for an example titration schedule of 2 mg twice a day.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "symptom" is a reference to one or more symptoms and equivalents thereof known to those skilled in the art, and so forth.

As used herein, the term "about" means plus or minus 10% of the numerical value of the number with which it is being used. Therefore, about 50 mL means in the range of 45 mL-55 mL.

The term "administering" or "administration" and the like, refers to providing the compositions of the invention (e.g. a composition according to any embodiment described herein) to a subject in need of treatment. Preferably the subject is a mammal, more preferably a human. The present invention comprises administering a pharmaceutical composition according to any embodiment described herein, alone or in conjunction with another therapeutic agent. When a composition according to any embodiment described herein, is administered in conjunction with another therapeutic agent, the pharmaceutical composition and the other therapeutic agent can be administered at the same time or different times.

"Serious adverse event" as used herein refers to any adverse event that (a) causes the subject discomfort and interrupts the subject's usual activities, (b) causes considerable interference with the subject's usual activities, and may be incapacitating or life threatening, (c) is life threatening to the subject, (d) results in dose limiting toxicity or (e) requires additional medication to combat the adverse event, or combinations thereof. For example, if the subject experiences nausea and/or vomiting upon administration of a huperzine pharmaceutical composition that requires the administration of an antiemetic in order to continue to take the huperzine pharmaceutical composition, the subject has a serious adverse event.

"Amyloid-related disorders" as used herein, include diseases associated with the accumulation of amyloid which can either be restricted to one organ, "localized amyloidosis", or spread to several organs, "systemic amyloidosis". Secondary amyloidosis may be associated with chronic infection (such as tuberculosis) or chronic inflammation (such as rheumatoid arthritis), including a familial form of secondary amyloidosis which is also seen in Familial Mediterranean Fever (FMF) and another type of systemic amyloidosis found in long-term hemodialysis patients. Localized forms of amyloidosis include, without limitation, type II diabetes and any related disorders thereof, neurodegenerative diseases such as scrapie, bovine spongiform encephalitis, Creutzfeldt-Jakob disease, Alzheimer's disease, senile systemic amyloidosis (SSA), Cerebral Amyloid Angiopathy, Parkinson's disease, and prion protein related disorders (e.g. prion-related encephalopathies), and rheumatoid arthritis.

The phrase "better side effect profile" means that the side effect(s) or serious adverse event(s) experienced by the patient or group of patients upon treatment with the modified release pharmaceutical composition of huperzine (1) occur at a lower incidence, (2) occur for a shorter duration, and/or (3) occur with a lesser severity; when compared to immediate release pharmaceutical compositions of an equivalent dose of huperzine.

The term "$C_{max}$" is the peak plasma concentration of a drug after administration to a subject.

The term "dose" as used herein refers to the quantity of active compound, for example huperzine or huperzine A absent any inactive ingredients or salts.

As used herein, the term "effective amount" means the amount of a drug or pharmaceutical agent, or the amount of a combination of drugs or pharmaceutical agents that will elicit the biological or medical response of a tissue, system, animal or human that is being sought, for instance, by a researcher or clinician.

As used herein, the term "epilepsy" refers to a disorder of the brain characterized by an enduring predisposition to generate epileptic seizures and by the neurobiologic, cognitive, psychological, and social consequences of this condition. An epileptic seizure is a transient occurrence of signs and/or symptoms due to abnormal excessive or synchronous neuronal activity in the brain.

It will be understood by one of skill in the art that the term "plasticized ethylcellulose" is also known by non-proprietary names, for example, "plasticized ethyl cellulose"; synonyms and several brand names, for example, SuRelease®.

It will be understood by one of skill in the art that the term "hydroxyproyl methylcellulose" is also known by many non-proprietary names, for example, "HPMC", "hypromellose", "hydroxypropylmethylcellulose", "hypromellosum", and "hypromellose"; synonyms; and several branded names, for example, Methocel™.

The term "huperzine" means huperzine A, huperzine B, or huperzine C, or their pharmaceutically accepted salts or solvates thereof, unless otherwise defined in a particular embodiment. Huperzine A is (1R,9S,13E)-1-amino-13-ethylidene-11-methyl-6-azatricyclo[7.3.1.02,7]trideca-2(7),3,10-trien-5-one. Huperzine B is (4aR,5R,10bR)-2,3,4,4a,5,6-hexahydro-12-methyl-1H-5,10b-propeno-1,7-phenanthrolin-8(7H)-one. Huperzine C is (1R,9S,13R)-1-amino-13-ethenyl-11-methyl-6-azatricyclo[7.3.1.2,7]trideca-2(7),3,10-trien-5-one.

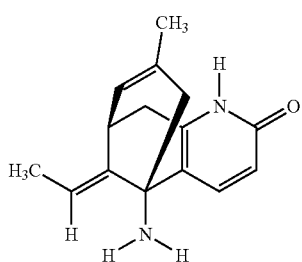

Huperzine A

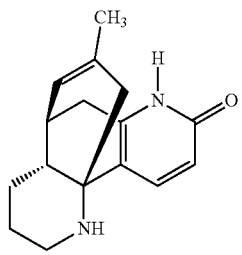

Huperzine B

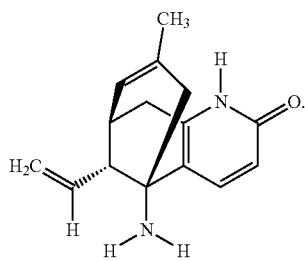

Huperzine C

Preferably, huperzine is huperzine A in any embodiment described herein.

The term "maintenance dose" as described herein refers to a dose of huperzine that administered to maintain a desired level of the medication in the blood. In some embodiments the maintenance dose is the therapeutically effect amount.

The term "modified release pharmaceutical composition of huperzine" refers to any oral pharmaceutical composition of huperzine wherein the huperzine-release characteristics of time, course and/or location are chosen to accomplish therapeutic or convenience objectives not offered by immediate release huperzine.

The term "neurological disorder" includes, but is not limited to, seizure disorders, an amyloid-related disorder such as Alzheimer's disease and the amyloid-disorders described herein, psychiatric disorders such as Tourette's syndrome, posttraumatic stress disorder (PTSD), panic and anxiety disorders, obsessive-compulsive disorder, and schizophrenia, developmental disorders such as fragile X syndrome and autism, pain, drug addictions such as alcoholism, neurodegenerative diseases such as Parkinson's disease and Huntington's disease, as well as stroke and ischemic brain injury, amyotrophic lateral sclerosis, and epilepsy. "Neurological disorder" also includes any disorder, symptom, or effect associated with or relating to exposure to a neurotoxin, including but not limited to neurotoxins such as chemical warfare agents.

The term "patient" or "subject" are used interchangeably and is used throughout the specification within context to describe an animal, generally a mammal and preferably a human, to whom treatment, including prophylactic treatment (prophylaxis), with the pharmaceutical compositions according to any embodiment described herein. For treatment of those infections, conditions or disease states which are specific for a specific animal such as a human patient, the term patient refers to that specific animal.

By "pharmaceutically-acceptable" it is meant that the carrier, diluent or excipient must be compatible with the other ingredients of the pharmaceutical composition and not deleterious to the recipient thereof.

The term "pharmaceutically acceptable salt of huperzine that is equivalent to about 1 weight % huperzine" refers to a pharmaceutically acceptable salt of huperzine that would provide about 1 weight % of huperzine free base if the salt was converted to huperzine. Similarly the terms "pharmaceutically acceptable salt that is equivalent to about 0.5 weight % to about 1.5 weight % huperzine", "pharmaceutically acceptable salt that is equivalent to about 0.9 weight % to about 1 weight % huperzine", "pharmaceutically acceptable salt that is equivalent to about 0.95 weight % to about 1 weight % huperzine" and the like refer to a pharmaceutically acceptable salt of huperzine that would provide about 0.5 weight % to about 1.5 weight %, about 0.9 weight % to about 1 weight %, about 0.95 weight % to about 1 weight %, huperzine free base respectively, if the salt was converted to huperzine. For example 6 grams of huperzine A is needed to provide 1 weight % of a 600 g pharmaceutical composition, but 6.89 g of the HCl salt of huperzine A is needed to provide 1 weight % huperzine A.

It will be understood by one of skill in the art that the term "polyvinylpyrrolidone" is also known by several non-proprietary names, for example, "PVP" "polyvinyl pyrrolidone", "povidone", and "polyvidone". It will also be understood that polyvinylpyrrolidones are referred to by their k number which indicates the mean molecular weight of the polyvinylpyrrolidone. Examples of polyvinylpyrrolidones include, but is not limited to polyvinylpyrrolidone K30, polyvinylpyrrolidone K10, polyvinylpyrrolidone K360, polyvinylpyrrolidone K40.

As used herein, the term "seizure disorder" means any condition in which one or more seizures is a symptom. As used herein, a seizure may be due to unusual electrical activity in the brain or may be a non-epileptic seizure, which is not accompanied by abnormal electrical activity in the brain. A seizure may be caused by, for example, but not limited to, psychological issues, psychological stress, trauma, hypoglycemia, low blood sodium, fever, alcohol use, or drug use or unknown causes. Types of seizures and seizure disorders include, but are not limited to, epilepsy (including intractable epilepsy), generalized seizures, primary generalized seizures, absence seizures, myoclonic seizures, partial seizures, complex partial seizures with or without generalization (for example, focal impaired awareness seizures (FIAS)), Lennox-Gastaut Syndrome, Dravet Syndrome and Generalized Epilepsy with Febrile Seizures plus (GEFS+). In some embodiments, the seizure disorder is epilepsy.

As used herein, the term "therapeutic" means an agent utilized to treat, combat, ameliorate, prevent, or improve an unwanted condition or disease of a patient. In part, embodiments of the present invention are directed to the treatment of neurodegenerative disorders including seizure disorders such as epilepsy.

The term "therapeutically effective amount" means any amount which results in improved treatment, healing, prevention, or amelioration of a disease, disorder, or side effect, or a decrease in the rate of advancement of a disease or disorder. The term also includes within its scope amounts effective to enhance normal physiological function.

The term "$t_{1/2}$" is the time it takes for the peak plasma concentration to reach half of its original value after administration to a subject.

By "$t_{max}$" it is meant the time to reach $C_{max}$ after administration to a subject.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

In some embodiments, the compounds and methods disclosed herein can be utilized with or on a subject in need of such treatment, which can also be referred to as "in need thereof." As used herein, the phrase "in need thereof" means that the subject has been identified as having a need for the particular method or treatment and that the treatment has been given to the subject for that particular purpose.

Generally speaking, the term "tissue" refers to any aggregation of similarly specialized cells which are united in the performance of a particular function.

The embodiments set forth herein are described in terms of "comprising", however any embodiment described herein may also be described in terms of "consists of" or "consisting of", meaning that the pharmaceutical composition or method includes only the elements, steps, or ingredients specifically recited in the particular claimed embodiment or claim and each of the embodiments described herein, may also be described in terms of "consisting essentially of" or "consists essentially of", meaning that the pharmaceutical composition or method includes only the specified materials or steps and those that do not materially affect the basic and novel characteristics of the claimed invention.

Pharmaceutical Compositions

Embodiments of the present invention relate to modified release, oral, pharmaceutical compositions of huperzine, and more particularly to huperzine A. Applicants have discovered modified release pharmaceutical compositions of huperzine that provide therapeutically effective plasma concentrations of huperzine, with twice daily dosing, and overcome the rapid high serum peak levels associated with the serious adverse (and dosing limiting) side effects of huperzine.

Figure 2:
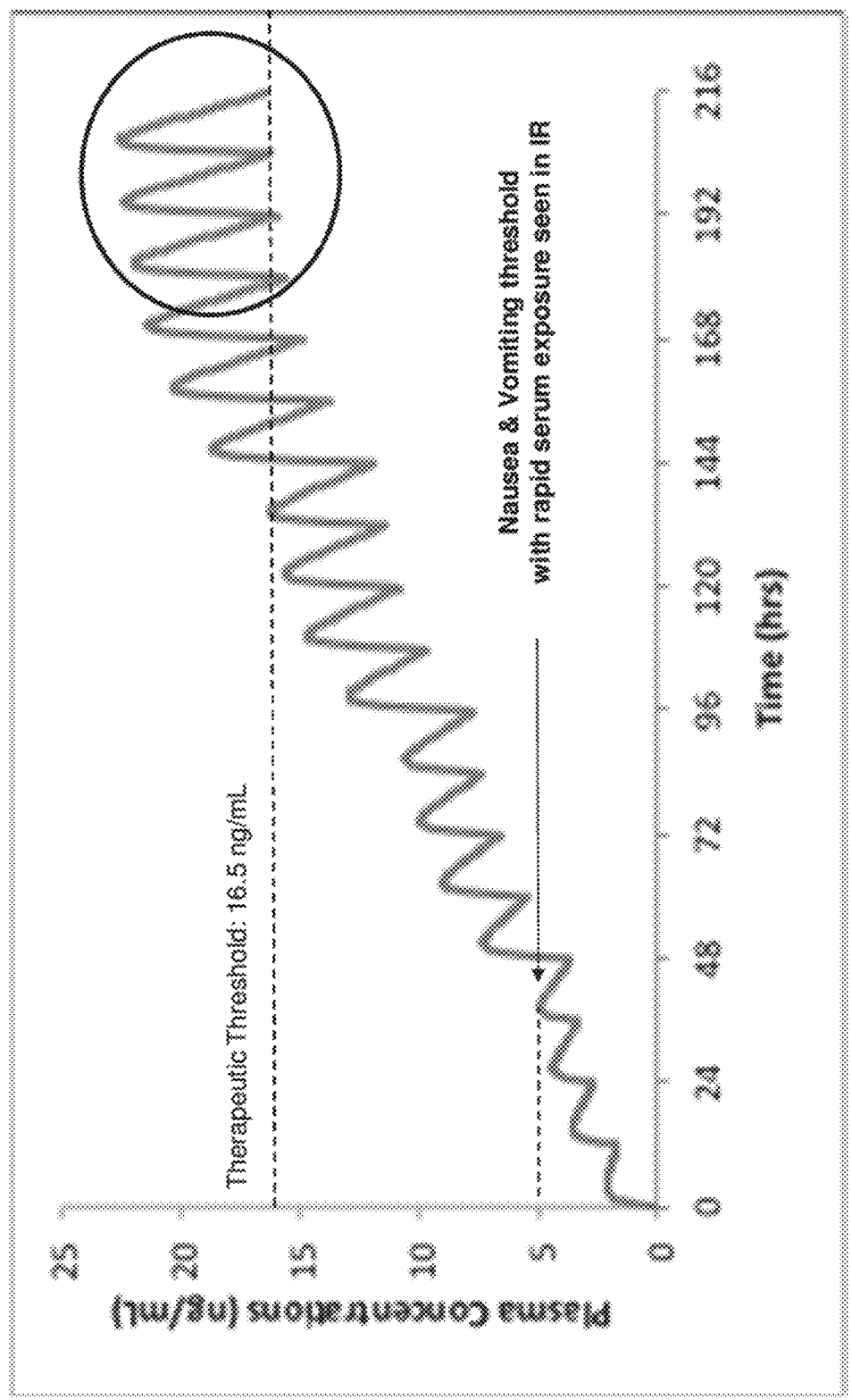
FIG. 2 shows the modeled plasma levels of huperzine A modified release pharmaceutical composition 4A based on a titration schedule of 0.5 mg huperzine A twice a day for days 1-2; 1 mg huperzine A twice a day for days 3-4; 1.5 mg huperzine twice a day for days 5-6 and 2 mg twice a day for days 7-11
Figure 3:
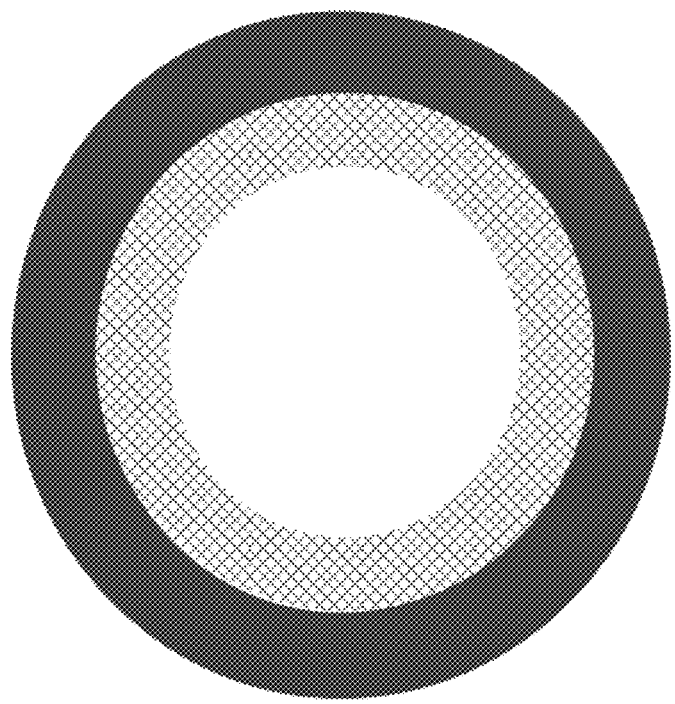
FIG. 3 is a schematic of the compositions of the invention. The white inner circle is the sugar sphere, the middle circle is the huperzine layer and the outer circle is the plasticized ethyl cellulose polymer.

To illustrate the advantages of a modified release pharmaceutical composition of huperzine A in treating, for example, seizure disorders, applicant used non clinical animal data, applicant generated pharmacokinetics in dogs (vide infra), allometric scaling, and modeling to determine that a therapeutic threshold ($C_{max}$) of about 16.5 ng/mL (2 mg dose) of huperzine A in serum is predicted to achieve efficacy in treating subjects with seizure disorders. However, a dose escalation study conducted by the applicant (unpublished), indicated that high serum peak levels greater than about 5 ng/mL especially within the first 31 hours have a high probability of resulting in nausea and vomiting. In the study, 7 out of 8 subjects experienced nausea and/or vomiting within the first 31 hrs. These subjects had an average time to initial nausea of 17.7 hours, and displayed huperzine plasma levels of 4.8 ng/mL on average. The one subject that did not experience nausea did not reach plasma levels of over 5 ng/mL until 42 hours after initial dosing. These findings would indicate that there is a time-concentration relationship, where achieving plasma exposures between 4-5 ng/mL within the first 31 hours may result in drug-related adverse events. Prior to Applicant's immediate release dose escalation study, it was unknown what plasma concentration threshold to stay below in order to obtain a better side effect profile. Dosing of about 2 mg immediate release huperzine A twice a day therefore is predicted to cause early, high serum peaks associated with nausea and vomiting. Additionally, peak to trough serum exposures are predicted to fluctuate below the therapeutic threshold. Furthermore, a single missed dose of huperzine is predicted to not only put the subject below the therapeutic threshold, but also expose the subject to rapid, high peak serum concentration upon resuming the immediate release dose, thus potentially resulting in nausea and vomiting each time a dose is missed (FIG. 1). This makes the immediate release pharmaceutical composition unfavorable and potentially dangerous as a therapeutic option. In contrast, the modified release pharmaceutical compositions developed by the applicant and administered as described herein, achieved the therapeutic threshold and unlike immediate release pharmaceutical compositions, keep serum exposure levels below the 5 ng/mL threshold initially, thereby avoiding the adverse nausea and vomiting associated with the immediate release pharmaceutical compositions. In addition, if, after reaching the therapeutic level, a subject misses a dose, the plasma concentration will not fall so low that the serious adverse events will occur (FIG. 2).

Applicant has discovered oral pharmaceutical modified release pharmaceutical compositions of huperzine that offer unexpected properties over other oral pharmaceutical compositions of huperzine. These pharmaceutical compositions allow for higher therapeutic thresholds to be obtained without the side effects associated with high serum peak levels and also allow for twice daily dosing.

In embodiments, orally administrable, modified release pharmaceutical compositions of huperzine of the present invention comprise a dissolvable core; a huperzine layer coating the dissolvable core; and a polymer coating, coating the huperzine layer; wherein the huperzine layer comprises a therapeutically-effective amount of huperzine.

In some embodiments of the invention, the dissolvable core is a fully dissolvable core. In further embodiments, the core is a sugar sphere. In some embodiments, the sugar sphere comprises sucrose and starch. In some embodiments, the sucrose is at least 62% by weight sucrose. In further embodiments, the sugar spheres are Suglets® sugar spheres. In some embodiments, the sugar spheres are of a particle size of about 250 µm to about 1700 µm. In some embodiments, the sugar spheres are selected from a particle size of about 250 µm to about 355 µm, about 500 µm to about 600 µm, about 600 µm to about 710 µm, about 710 µm to about 850 µm, about 850 µm to about 1000 µm, about 850 µm to about 1180 µm, about 1000 µm to about 1180 µm, about 1000 µm to about 1400 µm, about 1400 µm to about 1700 µm and combinations thereof. In further embodiments, the sugar spheres are selected from a particle size of about 500 µm to about 600 µm, or about 600 µm to about 710 µm. In some embodiments, the sugar spheres are selected from a particle size of about 500 µm to about 710 µm. In some embodiments, the sugar spheres are Suglets® PF006.

In further embodiments, the sugar sphere comprises about 74 weight % to about 86 weight % of the pharmaceutical composition. In some embodiments, the sugar sphere comprises about 79 weight % to about 84 weight % of the pharmaceutical composition. In some embodiments, the sugar sphere comprises about 80 weight % to about 86 weight % of the pharmaceutical composition. In some embodiments the sugar sphere comprises about 80 weight % to about 83 weight % of the pharmaceutical composition. In some embodiments the sugar sphere comprises about 81 weight % to about 83 weight % of the pharmaceutical composition. In some embodiments the sugar sphere comprises about 81 weight % to about 82.8 weight % of the pharmaceutical composition. In some embodiments the sugar sphere comprises 81.5 weight % to 83.0 weight %. In some embodiments the sugar sphere comprises about 79.1 weight % to about 80 weight % of the pharmaceutical composition. In some embodiments the sugar sphere comprises about 80 weight % to about 81 weight % of the pharmaceutical composition. In some embodiments the sugar sphere comprises about 81 weight % to about 82 weight % of the pharmaceutical composition. In some embodiments the sugar sphere comprises about 81 weight % to about 81.9 weight % of the pharmaceutical composition. In some embodiments the sugar sphere comprises about 81.9 weight % to about 82.8 weight % of the pharmaceutical composition. In some embodiments the sugar sphere comprises about 82 weight % to about 83 weight % of the pharmaceutical composition. In some embodiments the sugar sphere comprises about 82.8 weight % to about 83.7 weight % of the pharmaceutical composition.

In some embodiments the weight percent of sugar sphere in the pharmaceutical composition is between a lower limit of about 74 weight %, about 75 weight %, about 76 weight %, about 77 weight %, 78 about weight %, about 79 weight %, about 80 weight %, about 81 weight %, about 82 weight %, about 83 weight %, about 84 weight %, about 85 weight %, and about 86 weight % and an upper limit of about 86 weight %, about 85 weight %, about 84 weight %, 83 weight %, 82 weight %, 81 weight %, 80 weight %, 79 weight %, 78 weight %, 77 weight %, 76 weight %, 75 weight %, and 74 weight %.

In some embodiments the weight percent of sugar sphere in the pharmaceutical composition is about 74 weight %, about 75 weight %, about 76 weight %, about 77 weight %, about 78 weight %, about 79 weight %, about 80 weight %, about 81 weight %, about 82 weight %, about 83 weight %, about 84 weight %, about 85 weight %, or about 86 weight %.

In some embodiments of the invention, the huperzine layer comprises huperzine A or pharmaceutically acceptable salts thereof. In some embodiments the huperzine A is a *Huperzia serrata* extract. In some embodiments the *Huperzia serrata* extract is about 99% huperzine A.

In some embodiments, the weight percent of huperzine in the pharmaceutical composition comprises about 0.5 weight % to about 1.5 weight % huperzine or a pharmaceutically acceptable salt of huperzine that is equivalent to 0.5 weight % to about 1.5 weight % huperzine. In some embodiments, the weight percent of huperzine in the pharmaceutical composition comprises about 0.9 weight % to about 1 weight % huperzine or a pharmaceutically acceptable salt of huperzine that is equivalent to 0.9 weight % to about 1 weight % huperzine. In some embodiments, the weight percent of huperzine in the pharmaceutical composition comprises about 0.95 weight % to about 1 weight % huperzine or a pharmaceutically acceptable salt of huperzine that is equivalent to 0.95 weight % to about 1 weight % huperzine. In some embodiments, the weight percent of huperzine in the pharmaceutical composition comprises about 1 weight % huperzine or a pharmaceutically acceptable salt that is equivalent to about 1 weight % huperzine. In some embodiments the weight percent of huperzine in the pharmaceutical composition comprises between a lower limit of about 0.5 weight %, about 0.6 weight %, about 0.7 weight %, about 0.8 weight %, 0.9 about weight %, about 1 weight %, about 1.1 weight %, about 1.2 weight %, about 1.3 weight %, about 1.4 weight %, and about 1.5 weight % and an upper limit of about 1.5 weight %, about 1.4 weight %, about 1.3 weight %, 1.2 weight %, 1.1 weight %, 1 weight %, 0.9 weight %, 0.8 weight %, 0.7 weight %, 0.6 weight, and 0.5 weight % of huperzine or a pharmaceutically acceptable salt of huperzine that is equivalent to a lower limit of about 0.5 weight %, about 0.6 weight %, about 0.7 weight %, about 0.8 weight %, 0.9 about weight %, about 1 weight %, about 1.1 weight %, about 1.2 weight %, about 1.3 weight %, about 1.4 weight %, and about 1.5 weight % and an upper limit of about 1.5 weight %, about 1.4 weight %, about 1.3 weight %, 1.2 weight %, 1.1 weight %, 1 weight %, 0.9 weight %, 0.8 weight %, 0.7 weight %, 0.6 weight, and 0.5 weight % of huperzine. In some embodiments the weight percent of huperzine in the pharmaceutical composition comprises 0.5 weight %, about 0.6 weight %, about 0.7 weight %, about 0.8 weight %, 0.9 about weight %, about 1 weight %, about 1.1 weight %, about 1.2 weight %, about 1.3 weight %, about 1.4 weight %, and about 1.5 weight % or a pharmaceutically acceptable salt of huperzine that is equivalent to 0.5 weight %, about 0.6 weight %, about 0.7 weight %, about 0.8 weight %, 0.9 about weight %, about 1 weight %, about 1.1 weight %, about 1.2 weight %, about 1.3 weight %, about 1.4 weight %, and about 1.5 weight % of huperzine. In further embodiments, the huperzine layer comprises a therapeutically-effective amount of huperzine.

In some embodiments, the huperzine layer further comprises one or more excipients. In some embodiments, the total amount of excipients is about 5 weight % to about 10 weight % of the pharmaceutical composition. In some embodiments the total amount of excipients is about 5 weight % to about 9 weight % of the pharmaceutical composition. In some embodiments the total amount of excipients is about 5 weight % to about 7 weight % of the pharmaceutical composition. In some embodiments the total amount of excipients in the huperzine layer is selected from about 5 weight %, about 6 weight %, about 7 weight %, about 8 weight %, about 9 weight %, or about 10% weight %, of the pharmaceutical composition. In some embodiments, the excipients are selected from hydroxypropyl methylcellulose or polyvinylpyrrolidone and combinations thereof.

In some embodiments, the hydroxypropyl methylcellulose is a low viscosity or very low viscosity hydroxypropyl methylcellulose, such as, for example Methocel™ hydroxyproply methycelluloses. In further embodiments, the hydroxypropyl methylcellulose is Methocel VLV or the like. In some embodiments, the amount of hydroxypropyl methylcellulose in the huperizine layer is about 6 weight % to about 7 weight % of the composition. In some embodiments, the amount of hydroxypropyl methylcellulose in the huperizine layer is about 5 weight % to about 6 weight % of the composition. In some embodiments, the amount of hydroxypropyl methylcellulose in the huperizine layer is about 6 weight %. In some embodiments, the amount of hydroxypropyl methylcellulose in the huperizine layer is about 5 weight %. In further embodiments, the hydroxypropyl methylcellulose is Methocel VLV and the amount of Methocel VLV in the huperizine layer is about 6.1 weight % of the composition.

In some embodiments of the invention, the polyvinylpyrrolidone is any polyvinylpyrrolidone appropriate for use in an oral pharmaceutical composition. In further embodiments, the polyvinyl pyrrolidone is polyvinylpyrrolidone K30. In some embodiments, the amount of polyvinylpyrrolidone in the huperzine layer is about 0.5 weight % to about 1.5 weight % of the composition. In some embodiments, the polyvinylpyrrolidone in the huperzine layer is about 0.95 weight % to about 1 weight % of the composition. In some embodiments, the polyvinylpyrrolidone in the huperzine layer is about 0.90 weight % to about 1 weight % of the composition. In some embodiments, the polyvinylpyrrolidone in the huperzine layer is about 1 weight % of the composition. In further embodiments the polyvinylpyrrolidone is polyvinylpyrrolidone K30 and the amount of polyvinylpyrrolidone K30 in the huperzine layer is about 1 weight % of the composition.

In some embodiments the one or more excipients in the huperzine layer is a combination of hydroxypropyl methylcellulose and polyvinylpyrrolidone. In some embodiments the one or more excipients in the huperzine layer is of about 5 weight % to about 7 weight % hydroxypropyl methylcellulose and about 0.5 weight % to about 1.5 weight % polyvinylpryrrolidone. In some embodiments the one or more excipients in the huperzine layer is about 6 weight % hydroxypropyl methylcellulose and about 1 weight % polyvinylpryrrolidone.

In some embodiments of the invention, the polymer coating is a poly acrylamide polymer or ethylcellulose polymer layer coating the huperzine layer. In some embodiments the polymer coating is a non-polyacrylamide polymer coating the huperzine layer. In some embodiments the polymer coating is an a plasticized ethylcellulose polymer layer coating the huperzine layer. In further embodiments the plasticized ethylcellulose is a SuRelease® ethylcellulose. In some embodiments the plasticized ethylcellulose is SurRelease® Type B NF E.

In some embodiments the plasticized ethylcellulose polymer comprises about 7 weight % to about 16 weight % of the composition. In some embodiments the plasticized ethylcellulose polymer comprises about 8 weight % to about 13 weight % of the composition. In some embodiments the plasticized ethylcellulose polymer comprises about 7 weight % to about 12 weight % of the composition. In some embodiments the plasticized ethylcellulose polymer comprises about 8 weight % to about 12 weight % of the composition. In some embodiments the plasticized ethylcellulose polymer comprises about 9 weight % to about 11 weight % of the composition. In some embodiments the plasticized ethylcellulose polymer comprises about 9 weight % to about 10 weight % of the composition. In some embodiments the plasticized ethyl cellulose polymer comprises about 8.3 weight % to about 9.2 weight % of the pharmaceutical composition. In some embodiments the plasticized ethyl cellulose polymer comprises about 9.2 weight % to about 10.1 weight % of the pharmaceutical composition. In some embodiments the plasticized ethyl cellulose polymer comprises about 10.1 weight % to about 11 weight % of the pharmaceutical composition. In some embodiments the plasticized ethyl cellulose polymer comprises about 11 weight % to about 12 weight % of the pharmaceutical composition. In some embodiments the plasticized ethyl cellulose polymer comprises about 12 weight % to about 12.9 weight % of the pharmaceutical composition. In some embodiments the plasticized ethyl cellulose polymer comprises about 15 weight % to about 16 weight % of the pharmaceutical composition.

In some embodiments, the weight percent of plasticized ethylcellulose polymer in the composition is between a lower limit of 7 weight %, 8 weight %, 9 weight %, 10 weight %, 11 weight %, 12 weight %, 13 weight %, 14 weight %, 15 weight %; and 16 weight % and an upper limit of 16 weight %, 15 weight %, 14 weight %; 13 weight %, 12 weight %, 11 weight %, 10 weight %, 9 weight %, 8 weight % and 7 weight %.

In some embodiments, the pharmaceutical composition comprises:
a) a dissolvable core according to any embodiment described herein for dissolvable cores;
b) a huperzine layer comprising huperzine or a pharmaceutically acceptable salt of huperzine, according to any embodiment described herein for the huperzine layer, coating the dissolvable core; and
c) a polymer coating, coating the huperzine layer, according to any embodiment described herein.

In some embodiments of the invention the pharmaceutical composition for oral delivery comprises: (a) about 74 weight % to about 86 weight % of a sugar sphere core wherein the sugar sphere core has a particle size of about 500-710 μm; (b) a huperzine layer coating the sugar sphere, wherein the huperzine layer comprises about 0.95% to about 1 weight % huperzine or a pharmaceutically acceptable salt of huperzine that is equivalent to about 0.95% to about 1 weight % huperzine, and one or more excipients, wherein the total amount of excipients is about 5 weight % to about 9 weight %, (c) about 7 weight % to about 16 weight % of a plasticized ethyl cellulose polymer layer coating the huperzine layer, wherein the huperzine layer comprises a therapeutically-effective amount of huperzine. In further embodiments, the huperzine is huperzine A. In further embodiments the one or more excipients is a combination of hydroxypropyl methylcellulose and polyvinylpyrrolidone. In further embodiments the one or more excipients is a combination of about 6 weight % hydroxypropyl methylcellulose and about 1 weight % polyvinylpyrrolidone. In some embodiments the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E.

In some embodiments of the invention the pharmaceutical composition comprises: (a) about 79 weight % to about 84 weight % of a sugar sphere core wherein the sugar sphere core has a particle size of about 500-710 μm; (b) a huperzine layer coating the sugar sphere, wherein the huperzine layer comprises about 0.95 weight % to about 1 weight % huperzine or a pharmaceutically acceptable salt of huperzine that is equivalent to about 0.95 weight % to about 1 weight % of huperzine, about 6 weight % hydroxypropyl methylcellulose, and 0.95% to about 1 weight % polyvinylpyrrolidone; and (c) about 8 weight % to about 13 weight % of a plasticized ethyl cellulose polymer layer coating the huperzine layer, wherein the huperzine layer comprises a therapeutically-effective amount of huperzine. In further embodiments, the huperzine is huperzine A. In further embodiments, the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E., the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E.

In some embodiments of the invention the pharmaceutical composition comprises: (a) about 80 weight % to about 83 weight % of a sugar sphere core wherein the sugar sphere core has a particle size of about 500-710 μm; (b) a huperzine layer coating the sugar sphere, wherein the huperzine layer about 0.95 weight % to about 1 weight % huperzine or a pharmaceutically acceptable salt of huperzine that is equivalent to about 0.95 weight % to about 1 weight % huperzine, about 5 weight % to about 6 weight % hydroxypropyl methylcellulose, and about 0.95 weight % to about 1 weight % polyvinylpryrrolidone; and (c) about 8 weight % to about 12 weight % of a plasticized ethyl cellulose polymer layer coating the huperzine layer, wherein the huperzine layer comprises a therapeutically-effective amount of huperzine. In further embodiments, the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E.

In some embodiments of the invention the pharmaceutical composition comprises: (a) about 81 weight % to about 82 weight % of a sugar sphere core wherein the sugar sphere core has a particle size of about 500-710 μm; (b) a huperzine layer coating the sugar sphere, wherein the huperzine layer comprises about 0.95 weight % to about 1 weight % huperzine or a pharmaceutically acceptable salt of huperzine that is equivalent to about 0.95 weight % to about 1 weight % of huperzine, about 5 weight % to about 6 weight % hydroxypropyl methylcellulose, and about 0.95 weight % to about 1 weight % polyvinylpryrrolidone; and (c) about 10 weight % to about 11 weight % of a plasticized ethyl cellulose polymer layer coating the huperzine layer, wherein the huperzine layer comprises a therapeutically-effective amount of huperzine. In further embodiments, the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E.

In some embodiments of the invention the pharmaceutical composition comprises: (a) about 81.5 weight % of a sugar sphere core wherein the sugar sphere core has a particle size of about 500-710 μm; (b) a huperzine layer coating the sugar sphere, wherein the huperzine layer comprises about 1 weight % huperzine or a pharmaceutically acceptable salt of huperzine that is equivalent to 1 weight % of huperzine, about 5.9 weight % hydroxypropyl methylcellulose, and about 1 weight % polyvinylpryrrolidone; and (c) about 10.7 weight % of a plasticized ethyl cellulose polymer layer coating the huperzine layer, wherein the huperzine layer comprises a therapeutically-effective amount of huperzine. In further embodiments, the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E.

In some embodiments of the invention the pharmaceutical composition comprises: (a) about 82 weight % to about 83 weight % of a sugar sphere core wherein the sugar sphere core has a particle size of about 500-710 μm; (b) a huperzine layer coating the sugar sphere, wherein the huperzine layer comprises about 0.95 weight % to about 1 weight % huperzine or a pharmaceutically acceptable salt of huperzine that is equivalent to about 0.95 weight % to about 1 weight % of huperzine, about 5 weight % to about 6 weight % hydroxypropyl methylcellulose, and about 0.95 weight % to about 1 weight % polyvinylpryrrolidone; and (c) about 9 weight % to about 10 weight % of a plasticized ethyl cellulose polymer layer coating the huperzine layer, wherein the huperzine layer comprises a therapeutically-effective amount of huperzine. In further embodiments, the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E.

In some embodiments of the invention the pharmaceutical comprises: (a) about 83 weight % of a sugar sphere core wherein the sugar sphere core has a particle size of about 500-710 μm; (b) a huperzine layer coating the sugar sphere, wherein the huperzine layer comprises about 1 weight % huperzine or a pharmaceutically acceptable salt of huperzine that is equivalent to 1 weight % of huperzine, about 6 weight % hydroxypropyl methylcellulose, and about 1 weight % polyvinylpryrrolidone; and (c) about 9 weight % of a plasticized ethyl cellulose polymer layer coating the huperzine layer, wherein the huperzine layer comprises a therapeutically-effective amount of huperzine. In further embodiments, the the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E.

In some embodiments of the invention the pharmaceutical composition further comprises a seal coat layer in between the huperzine layer and the plasticized ethyl cellulose layer.

Some embodiments describe a pharmaceutical composition comprising: (a) about 75 weight % to about 76 weight % of a sugar sphere core wherein the sugar sphere core has a particle size of about 500-710 μm; (b) a huperzine layer coating the sugar sphere, wherein the huperzine layer comprises about 0.9 weight % to about 1 weight % huperzine or a pharmaceutically acceptable salt of huperzine that is equivalent to about 0.9 weight % to about 1 weight % of huperzine, about 5 weight % to about 6 weight % hydroxypropyl methylcellulose, and about 0.9 weight % to about 1 weight % polyvinylpryrrolidone; (c) a seal coat layer coating the huperzine layer, comprising about 1 weight % to about 2 weight % hydroxypropylmethyl cellulose; and (d) about 15 weight % to about 16 weight % of a plasticized ethyl cellulose polymer layer coating the huperzine layer, wherein the huperzine layer comprises a therapeutically-effective amount of huperzine. In further embodiments, the the huperzine is huperzine A, the hydroxypropyl methylcellulose is a low viscosity hydroxypropyl methylcellulose, the polyvinylpyrrolidone is a polyvinylpyrrolidone K30 and the plasticized ethyl cellulose is SurRelease® Type B NF E.

Embodiments of the present invention comprise a pharmaceutical composition according to any embodiment described herein, characterized by a $C_{max}$ of huperzine in plasma of about 4 ng/mL to about 8 ng/mL, a $T_{max}$ of about 4 hour to about 8 hours and a $t_{1/2}$ of about 8 hours to about 12 hours, upon oral administration of a therapeutically effective dose of the pharmaceutical composition to a human subject. In one embodiment the $C_{max}$ is about 4 ng/mL to about 6 ng/mL, $T_{max}$ is about 4 hours to about 8 hours and the $t_{1/2}$ is about 10 hours to about 12 hours. In one embodiment the $C_{max}$ is about 6 ng/mL, the $T_{max}$ is about 4 hours and the $t_{1/2}$ is about 8.3 hours.

Further embodiments of the invention encompass pharmaceutical composition according to any embodiment described herein, comprising a therapeutically-effective amount of huperzine, characterized by a $T_{max}$ of about 4 to about 8 hours and a $C_{max}$ that is reduced by about 25% to about 75% when compared with a $C_{max}$ of an immediate release huperzine pharmaceutical composition administered at an equivalent dose. In some embodiments the $C_{max}$ is reduced by 50% when compared with a $C_{max}$ of an immediate release huperzine pharmaceutical composition.

Some embodiments describe a pharmaceutical compositions according to any embodiment described herein, that exhibits the following dissolution profile when tested according to USP 1 type apparatus at 50 revolutions per minute in 50 mM phosphate (pH 6.8) at 37° C.: about 36% to about 46% of the huperzine is released after 2 hours, about 61% to about 77% of the huperzine is released after 4 hours, about 84% to about 97% of the huperzine is released after 8 hours and not less than about 89% of the huperzine is released after 12 hours.

Some embodiments describe a pharmaceutical compositions according to any embodiment described herein, that exhibits the following dissolution profile when tested according to USP 1 type apparatus at 50 revolutions per minute in 50 mM phosphate (pH 6.8) at 37° C.: about 36% of the huperzine is released after 2 hours, about 63% of the huperzine is released after 4 hours about 84% of the huperzine is released after 8 hours and not less than about 89% of the huperzine is released after 12 hours.

Some embodiments describe a pharmaceutical compositions according to any embodiment described herein, that exhibits the following dissolution profile when tested according to USP 1 type apparatus at 50 revolutions per minute in 50 mM phosphate (pH 6.8) at 37° C.: about 46% of the huperzine is released after 2 hours, about 77% of the huperzine is released after 4 hours about 97% of the huperzine is released after 8 hours and not less than about 99% of the huperzine is released after 12 hours.

Some embodiments describe a pharmaceutical compositions according to any embodiment described herein, that exhibits the following dissolution profile when tested according to USP 1 type apparatus at 50 revolutions per minute in 50 mM phosphate (pH 6.8) at 37° C.: about 43% of the huperzine is released after 2 hours, about 68% of the huperzine is released after 4 hours about 88% of the huperzine is released after 8 hours and not less than about 96% of the huperzine is released after 12 hours.

Some embodiments describe a pharmaceutical compositions according to any embodiment described herein, that exhibits the following dissolution profile when tested according to USP 1 type apparatus at 50 revolutions per minute in 50 mM phosphate (pH 6.8) at 37° C.: about 38% of the huperzine is released after 2 hours, about 61% of the huperzine is released after 4 hours about 84% of the huperzine is released after 8 hours and not less than about 94% of the huperzine is released after 12 hours.

Pharmaceutical compositions characterized by a plasma concentration of below 5 ng/mL maintained within the first 31 hours, upon oral administration of the pharmaceutical composition to a human subject are another embodiment of some embodiments of the invention.

In any embodiments described herein, the huperzine is huperzine A or pharmaceutically acceptable salts thereof. In any embodiments, the huperzine A is a *Huperzia serrata* extract. In any embodiments, the *Huperzia serrata* extract is about 99% huperzine A.

In any embodiments described herein, the pharmaceutical composition is for oral delivery. In embodiments, the pharmaceutical compositions of the invention are formulated for oral administration and can be, for example, in the form of tablets, sprinkles, capsules and pills. In one embodiment, the pharmaceutical compositions according to any embodiment described herein, are formulated for oral administration in the form of capsules. In some embodiments, the pharmaceutical compositions according to any embodiment described herein, are formulated for oral administration in the form of tablets. The compositions of the inventions can contain additional non-toxic pharmaceutically acceptable carriers and/or diluents and/or adjuvants and/or excipients.

The use of such media and agents for pharmaceutically active substances is well known in the art and includes tablet binders, lubricants, flavoring agents, preservatives, wetting agents, emulsifying agents, and dispersing agents.

As illustrated below and in the examples that follow, applicant has shown that the pharmaceutical compositions described in any of the embodiments described herein, have unexpected and unpredictable properties.

Applicant prepared a number of pharmaceutical compositions comprising an inert core layer, a huperzine layer coating the core layer and a polymer layer coating the huperzine layer as shown in Table 1.

TABLE 1

| Composition No. | Core type/Size* Weight % of total composition | Huperzine Layer** Weight % of each component in total composition | Seat coat layer Weight % of each component in total composition | Polymer layer Weight % of total composition |
|---|---|---|---|---|
| 1A | 76.10 MCC 500-710 μm | 5.48 HPMC 0.91 PVP 0.91 huperzine A | | 4.88 Eudragit RL 30 D 4.88 Eudragit RS 30 D 1.97 Triethyl citrate 4.88 Talc |
| 1B | 76.10 MCC 500-710 μm | 5.48 HPMC 0.91 PVP 0.91huperzine A | | 4.88 Eudragit RL 30 D 4.88 Eudragit RS 30 D 1.97 Triethyl citrate 4.88 Talc Eudragit, cured |
| 2A | 82.95 MCC 255-500 μm | 5.97 HPMC 1 PVP 1 huperzine A | | 9.09 SuRelease |
| 2B | 79.34 MCC 255-500 μm | 5.71 HPMC 0.95 PVP 0.95 huperzine A | | 13.04 SuRelease |
| 2C | 76.03 MCC 255-500 μm | 5.47 HPMC 0.91 PVP 0.91 huperzine A | | 16.67 SuRelease |
| 3A | 82.95 MCC 500-710 μm | 5.97 HPMC 1 PVP 1 huperzine A | | 9.09 SuRelease |
| 3B | 79.34 MCC 500-710 μm | 5.71 HPMC 0.95 PVP 0.95 huperzine A | | 13.04 SuRelease |
| 3C | 76.03 MCC 500-710 μm | 5.47 HPMC 0.91 PVP 0.91 huperzine A | | 16.67 SuRelease |
| 4A | 82.95 Sugar spheres 500-710 μm | 5.97 HPMC 1 PVP 1 Huperzine A | | 9.09 SuRelease |
| 4B | 79.34 Sugar spheres 500-710 μm | 5.71 HPMC 0.95 PVP 0.95 Huperzine A | | 13.04 SuRelease |
| 4D | 82.95 Sugar spheres 500-710 μm | 5.97 HPMC 1 PVP 1 Huperzine A | | 9.09 SuRelease |
| 4C | 91.24 Sugar spheres 500-710 μm | 6.57 HPMC 1.09 PVP 1.09 Huperzine A | | 0% |
| 4E | 75.81 Sugar spheres 500-710 μm | 5.46 HPMC 0.91 PVP 0.91 Huperzine A | 1.66 HPMC | 15.35 SuRelease |
| 4F-1 | 81.47 Sugar spheres 500-710 μm | 5.87 HPMC 0.98 PVP 0.98 Huperzine A | | 10.71 SuRelease |
| 4F-2 | 81.47 Sugar spheres 500-710 μm | 5.87 HPMC 0.98 PVP 0.98 Huperzine A | | 10.71 SuRelease |

Figure 4:
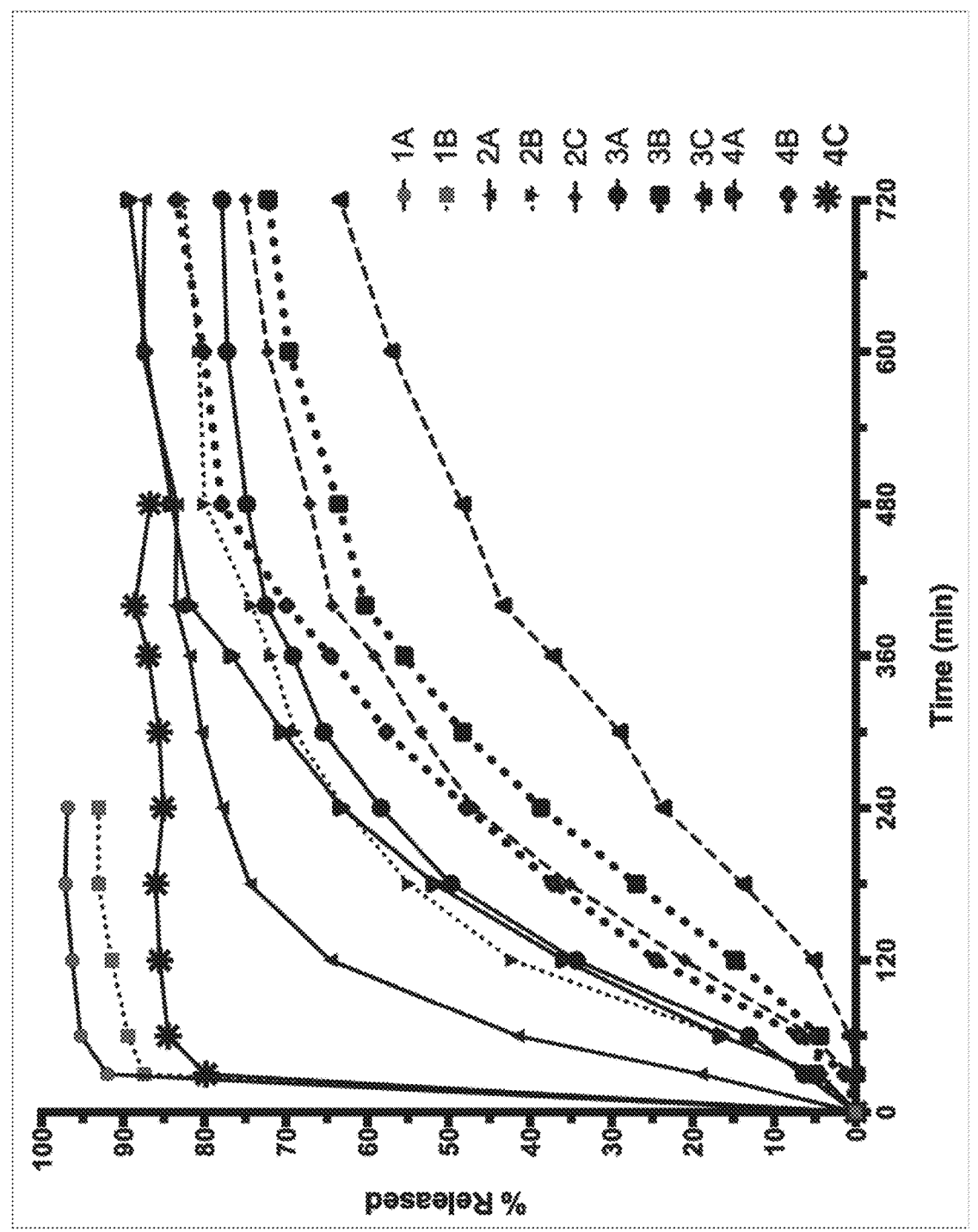
FIG. 4 shows the in vitro dissolution profile of pharmaceutical composition 1A (solid line with small circle), composition 1B (dashed line with small square), composition 2A (solid line with small triangle), composition 2B (dashed line with small triangle), composition 2C (solid line with small triangle), composition 3A (solid line with large circle), composition 3B (dashed line with large square), composition 3C (dashed line with large point up triangle), composition 4A (solid line with large, point down triangle), composition 4B (dashed line with small diamond), composition 4C (solid line with asterisk).
Figure 5:
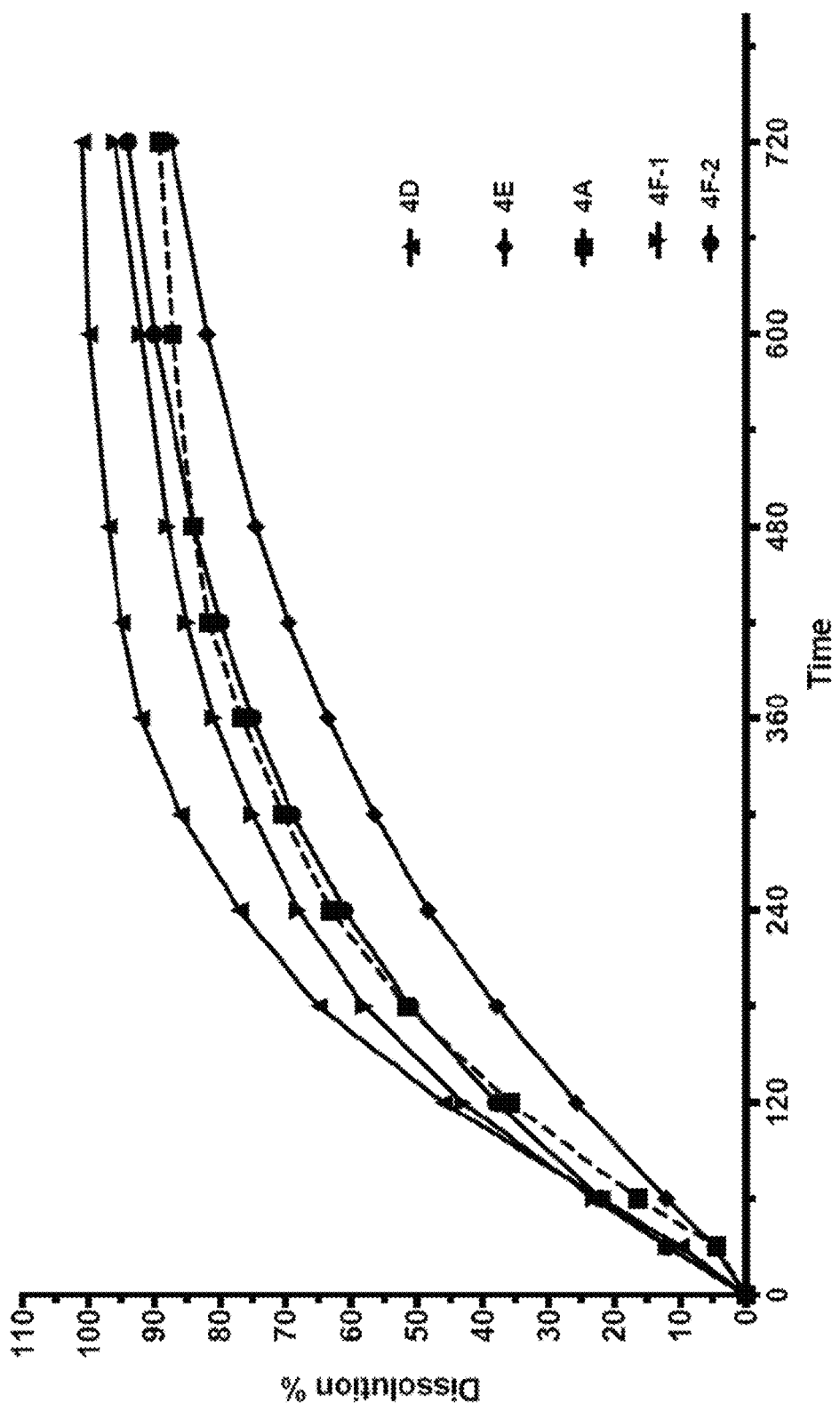
FIG. 5 shows the in vitro dissolution profile of composition 4D (solid line with upward pointing triangle), composition 4E (solid line with small diamond), composition 4A (large square with dashed line), composition 4F-1 (solid line with small triangle pointing downward), composition 4F-2 (solid line with circle).

*MCC = Microcrystalline cellulose spheres
**HPMC = hydroxypropylmethyl cellulose;
PVP = polyvinylpyrrolidone As illustrated in FIG. 4, compositions 1A and 1B had dissolution profiles that were so fast that they were more similar to immediate release pharmaceutical compositions than modified release pharmaceutical compositions, releasing 88-92% of the huperzine in about 30 minutes. This result is unexpected since microcrystalline cellulose spheres are known to one of skill in the art as suitable cores for extended/modified release of pharmaceuticals. Moreover, the MCC compositions 1A and 1B contained a Eudragit layer coating the huperzine layer. Eudragit would have been predicted to slow the rate of dissolution even further. Furthermore, given the dissolution profile of compositions 1 and 2, one of skill in the art would not have expected compositions comprising sugar spheres to offer advantages over the MCC spheres. Because sugar spheres are water soluble, one of skill in the art would expect the dissolution profile of a sugar sphere composition to be faster than compositions with the water insoluble MCC spheres. While the MCC compositions 2A, 2B, 2C, 3A, 3B, and 3C had longer release profiles, they either had an initial release that was too fast (rapid release), or they released too slowly. The sugar sphere compositions 4A, 4B, 4D, 4E, 4F-1, and 4F-2 and particularly 4D, 4F-1, and 4F-2, however, unexpectedly had a slow initial rate of dissolution and released about 85-90% (or higher) of huperzine after 12 hours, making them ideal for modified release pharmaceutical compositions of huperzine (See FIG. 5 and Table 2).

TABLE 2

| Time (min) | 4A | 4B | 4D | 4E | 4F-1 | 4F-2 |
|---|---|---|---|---|---|---|
| 0 | 0.0 | 0 | 0 | 0 | 0 | 0 |
| 30 | 4.5 | 1.4 | 10 | 4.9 | 12 | 12 |
| 60 | 16.5 | 7.0 | 22 | 12.1 | 23 | 22 |
| 120 | 35.8 | 24.5 | 46 | 25.8 | 43 | 38 |
| 180 | 51.7 | 37.2 | 65 | 37.9 | 58 | 51 |
| 240 | 63.2 | 47.8 | 77 | 48.3 | 68 | 61 |
| 300 | 70.5 | 57.7 | 86 | 56.5 | 75 | 69 |
| 360 | 76.6 | 64.6 | 92 | 63.6 | 81 | 75 |
| 420 | 81.8 | 69.9 | 95 | 69.6 | 85 | 80 |
| 480 | 84.0 | 77.9 | 97 | 74.6 | 88 | 84 |
| 600 | 87.2 | 80.1 | 100 | 82 | 92 | 90 |
| 720 | 89.3 | 83.5 | 101 | 87.4 | 96 | 94 |

Some embodiments describe a pharmaceutical composition according to any embodiment described herein, that exhibit a dissolution profile as defined in Table 2. In some embodiments, the dissolution profile has an F2 of greater than 50%, when compared to any of compositions 4A, 4D, 4F-1 and 4F-2. It will be understood by one of skill in the art that F2 is a factor that assesses the similarity of 2 dissolution curves and is represented by the formula $$F2 = 50 \times \log\{[1+(1/n)\Sigma(R-T)^2]^{-0.5} \times 100\}$$

where n is the number of time points being assessed, R=reference value at a given time, T=test value at equivalent time.

Figure 6:
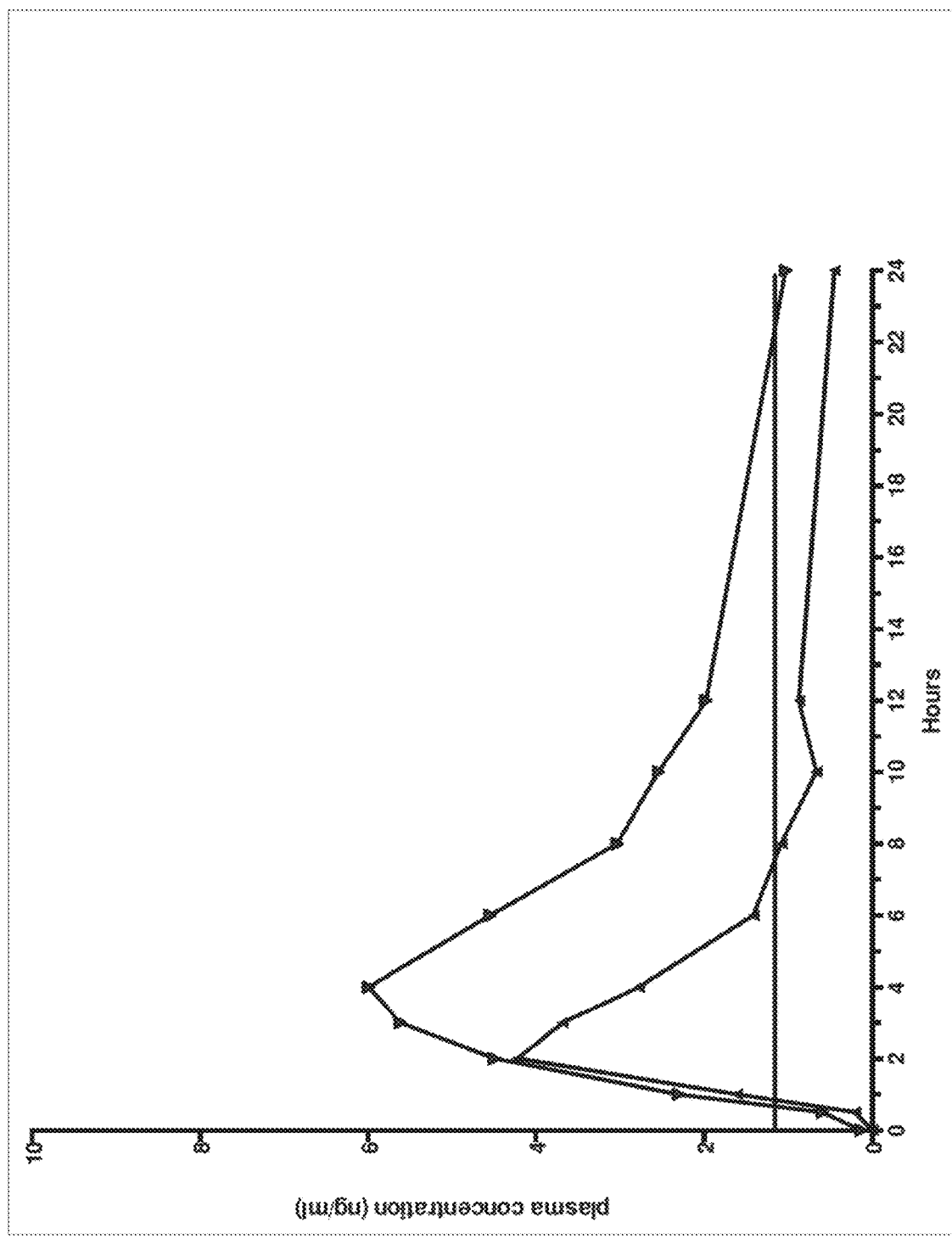
FIG. 6 shows the in vivo plasma concentration in dogs at a dose of 0.49 mg/kg for pharmaceutical composition 4A (solid line with point down triangle) and pharmaceutical composition 2C (solid line with point up triangle).

A pharmacokinetic study in dogs further illustrates the advantages of composition 4A, for example over the MCC compositions (See FIG. 6). The following pharmacokinetic parameters were observed in the study (See Table 3 and Example 2).

TABLE 3

| | Immediate Release* | Composition 4A | Composition 2C |
|---|---|---|---|
| $C_{max}$ ng/ml | 12.7 | 6.0 | 4.2 |
| $T_{max}$ (hours) | 1.25 | 4.0 | 2.0 |
| $T_{1/2}$ (hours) | 5.71 | 8.32 | 5.54 |

*based on values from Chu D, Liu W, Li Y, Li P, Gu J, Liu K. Pharmacokinetics of huperzine A in dogs following single intravenous and oral administrations. Planta Med. 2006 May; 72(6): 552-5,
**calculated based on equivalent dosing As illustrated in Table 3 and in FIG. 6, the MCC composition 2C, releases huperzine, however, the release and subsequent absorption of huperzine isn't fast enough to keep up with the clearance of the drug from the body, yielding only a minor prolongation of t ½ to 2 hours from 1.25 hours. Therefore, patients would have to receive huperzine in composition 2C four to six times daily, thus offering little advantage over immediate release pharmaceutical compositions. Composition 4A however, had a pharmacokinetic profile ideal for twice daily doing, demonstrating higher overall absorption, without clearing from the body too quickly.

A phase 1b clinical trial in humans, further illustrated that composition 4D had a favorable pharmacokinetic profile that showed a dramatic reduction of serious adverse events compared with the immediate release preparation, demonstrated twice a day dosing and demonstrated achievable drug plasma levels predicted to provide significant protection in patients that require higher doses of huperzine, for example, patients with seizure disorders (See Example 3).

Methods of Treatment

The pharmaceutical compositions according to any embodiment described herein, are useful in treating neurological disorders and/or seizure disorders to a patient in need thereof. They can be administered therapeutically to treat, prevent, or slow the rate of onset of neuronal dysfunctions. Some embodiments describe methods of treating neurological disorders and/or seizure disorders. Some embodiments describe methods of treating neurological disorders selected from amyloid-related disorder such as Alzheimer's disease and the amyloid-disorders described herein, psychiatric disorders such as Tourette's syndrome, posttraumatic stress disorder (PTSD), panic and anxiety disorders, obsessive-compulsive disorder, and schizophrenia, developmental disorders such as fragile X syndrome and autism, pain, drug addictions such as alcoholism, neurodegenerative diseases such as Parkinson's disease and Huntington's disease, as well as stroke and ischemic brain injury, amyotrophic lateral sclerosis, epilepsy, and any disorder, symptom, or effect associated with or relating to exposure to a neurotoxin, including but not limited to neurotoxins such as chemical warfare, with a pharmaceutical composition according to any embodiment described herein.

In embodiments, the present invention provides methods of treating seizures or seizure disorders selected from epilepsy (including intractable epilepsy), generalized seizures, primary generalized seizures, absence seizures, myoclonic seizures, partial seizures, complex partial seizures with or without generalization (for example, focal impaired awareness seizures (FIAS)), Lennox-Gastaut Syndrome, Dravet Syndrome and Generalized Epilepsy with Febrile Seizures plus (GEFS+). In some embodiments, the seizure disorder is epilepsy.

The pharmaceutical compositions according to any embodiment described herein, can be administered therapeutically to treat, prevent, or slow the rate of onset of neuronal dysfunctions, such as epilepsy and seizures, or prophylactically to either protect against further seizures associated with epilepsy or to avoid or forestall the onset of seizures associated with other disorders. For example, the pharmaceutical compositions according to any embodiment described herein, can be administered prophylactically to slow or halt the progression of seizures and epilepsy in a patient who has had a stroke and has a risk of developing seizure as a result of the stroke.

Further embodiments describe methods of treating epilepsy, intractable epilepsy and FIAS, comprising administering to a patient in need thereof, a pharmaceutical composition according to any embodiment described herein.

In some embodiments the pharmaceutical compositions of the invention is administered at a dose to reduce seizures by at least 10% with a better side effect profile. Preferably, the reduction is 20%, 50%, 75% or eliminates seizure episodes. For example, the pharmaceutical compositions according to any embodiment described herein, prevents the development of or completely eliminates seizures.

In further embodiments, the present invention provides methods of treating any disorder, symptom, or effect associated with or relating to exposure to a neurotoxin, including but not limited to neurotoxins such as chemical warfare, comprising administering to a patient in need thereof, a pharmaceutical composition according to any embodiment described herein.

In some embodiments, the dose of huperzine in the pharmaceutical compositions of the invention preferably does not exceed 10 mg/day. In some embodiments, the dose preferably does not exceed 6.5 mg/day. In some embodiments, the dose is between a lower limit of about 0.01 mg/day, about 0.05 mg/day, about 0.1 mg/day, about 0.25 mg/day, about 0.5 mg/day, about 0.75 mg/day, about 0.8 mg/day, about 1 mg/day, about 1.1 mg/day, about 1.25 mg/day, about 1.5 mg/day, about 1.75 mg/day, about 2 mg/day, about 2.2 mg/day, about 2.25 mg/day, about 2.5 mg/day, about 3.0 mg/day, about 3.5 mg/day, about 4.0 mg/day, about 4.5 mg/day, about 5.0 mg/day, about 5.5 mg/day, about 6.0 mg/day and about 6.5 mg/day; and an upper limit of about 6.5 mg/day, about 6.0 mg/day, about 5.5 mg/day, about 5 mg/day, about 4.5 mg/day, about 4.0 mg/day, about 3.5 mg/day, about 3.0 mg/day, about 2.5 mg/day, about 2.25 mg/day, about 2.2 mg/day, about 2 mg/day, about 1.75 mg/day, about 1.5 mg/day, about 1.25 mg/day, about 1.1 mg/day, about 1 mg/day, about 0.75 mg/day, about 0.8 mg/day, about 0.5 mg/day, about 0.25 mg/day, about 0.1 mg/day, about 0.05 mg/day and about 0.01 mg/day. In some embodiments the dose is about 0.01 mg/day to about 0.8 mg/day. In further embodiments the dose is about 0.25 mg/day to about 5 mg/day. In some embodiments the dose is about 0.25 mg/day to about 0.5 mg/day. In some embodiments the dose is about 0.5 mg/day to about 0.75 mg/day. In some embodiments the dose is about 0.75 mg/day to about 1 mg/day. In some embodiments the dose is about 1 mg/day to about 1.25 mg/day. In some embodiments the dose is about 1.25 mg/day to about 1.5 mg/day. In some embodiments the dose is about 1.5 mg/day to about 1.75 mg/day. In some embodiments the dose is about 1.75 mg/day to about 2.0 mg/day. In some embodiments the dose is about 2.0 mg/day to about 2.25 mg/day. In some embodiments the dose is about 2.25 mg/day to about 2.5 mg/day. In some embodiments the dose is about 2.5 mg/day to about 2.75 mg/day. In some embodiments the dose is about 2.75 mg/day to about 3.0 mg/day. In some embodiments the dose is about 3.0 mg/day to about 3.25 mg/day. In some embodiments the dose is about 3.25 mg/day to about 3.50 mg/day. In some embodiments the dose is about 3.50 mg/day to about 3.75 mg/day. In some embodiments the dose is about 3.75 mg/day to about 4.0 mg/day. In some embodiments the dose is about 4.0 mg/day to about 4.25 mg/day. In some embodiments the dose is about 4.25 mg/day to about 4.5 mg/day. In some embodiments the dose is about 4.5 mg/day to about 4.75 mg/day. In some embodiments the dose is about 4.75 mg/day to about 5 mg/day. In some embodiments the dose is about 1 mg/day to about 5 mg/day. In some embodiments the dose is about 0.5 mg/day to about 5 mg/day. In some embodiments the dose is about 0.5 mg/day to about 2.2 mg/day. In some embodiments, the dose is about 5 mg/day. In some embodiments the dose is about 0.5 mg/day, about 1 mg/day, about 1.1 mg/day mg/day, about 1.5 mg/day, about 2.0 mg/day, about 2.50 mg/day, about 3.0 mg/day, about 3.5 mg/day or about 3.6 mg/day. In some embodiments the daily dose according to any embodiment described herein, is administered twice a day. In some embodiments the dose is about 0.25 mg twice a day to about 2.5 mg twice a day. In some embodiments the dose is about 0.25 mg twice a day, about 0.5 mg twice a day, about 0.75 mg twice a day, about 1.0 mg twice a day, about 1.1 mg twice a day, about 1.25 mg twice a day, 1.5 mg twice a day, 1.75 mg twice a day, 1.8 mg twice a day, 2.0 mg twice a day, 2.25 mg twice a day, or 2.5 mg twice a day.

In some embodiments, doses of about 0.05 mg/day to about 7 mg/day, about 05 mg/day to about 5 mg/day, about 0.05 mg/day to about 0.8 mg/day, about 0.05 mg/day to about 0.4 mg/day, about 0.05 mg/day to about 0.02 mg/day, or 0.05 mg/day to about 0.01 mg/day may also used. In some embodiments these doses may be used to treat any neurological disorder. In some embodiments these doses may be used to treat symptoms or effects associated with or relating to exposure to neurotoxins such as chemical warfare agents.

In some embodiments the present disclosure provides a method of treating a neurological and/or seizure disorder comprising administering to a patient in need thereof, one or more titration doses of an modified release pharmaceutical composition of huperzine, followed by a maintenance dose of an oral modified release pharmaceutical composition of huperzine, wherein the patient experiences a better side effect profile. In some embodiments, the modified release pharmaceutical composition of huperzine administered in the titration dose is the same modified release pharmaceutical composition of huperzine administered in the maintenance dose. In further embodiments, the modified release pharmaceutical composition of huperzine administered in the titration dose is different than the modified release pharmaceutical composition of huperzine administered in the maintenance dose. In further embodiments the huperzine is huperzine A. In some embodiments the modified release pharmaceutical composition of huperzine comprises a dissolvable core; an active huperzine A layer coating the dissolvable core; and a polymer coating, coating the huperzine A layer. In further embodiments, the modified release huperzine pharmaceutical composition is a pharmaceutical composition according to any embodiment described herein. In some embodiments, the modified release pharmaceutical composition of huperzine is a pharmaceutical composition according to any embodiment described herein, and is the same pharmaceutical composition in the titration dose and the maintenance dose. In some embodiments, the oral modified release pharmaceutical composition of huperzine is a pharmaceutical composition comprising huperzine A according to any embodiment described herein, and is the same pharmaceutical composition comprising huperzine A in the titration dose and the maintenance dose. In some embodiments, the dose is titrated from a low dose to high dose over several days to several weeks until a maintenance dose is reached.

Some embodiments describe a method of treating a neurological disorder and/or a seizure disorder, in a patient in need thereof, wherein the patient experiences a better side effect profile, comprising administering a first dosing regimen of at least one dosing regimen selected from a. to h. (as further described below) and administering a second dosing regimen of at least one dosing regimen selected from a. to i. (as further described below), provided the second dosing regimen ascends from the first dosing regimen and further provided the last dosing regimen is the maintenance dose and therefore will be administered for as long as the patient is in need of treatment thereof:
   a. administering a dose of about 0.01 mg to about 0.25 mg of huperzine, once every about 12 hours for at least two days and up to two weeks;
   b. administering a dose of about 0.26 mg to about 0.5 mg of huperzine, once every about 12 hours for at least two days and up to two weeks;

c. administering a dose of about 0.51 mg to about 0.75 mg of huperzine, once every about 12 hours for at least two days and up to two weeks;
d. administering a dose of about 0.76 mg to about 1 mg of huperzine, once every about 12 hours for at least two days and up to two weeks;
e. administering a dose of about 1.1 mg to about 1.25 mg of huperzine, once every about 12 hours for at least two days and up to two weeks;
f. administering a dose of about 1.26 mg to about 1.5 mg of huperzine, once every about 12 hours for at least two days and up to two weeks;
g. administering a dose of about 1.51 mg to about 1.75 mg of huperzine, once every about 12 hours for at least two days and up to two weeks;
h. administering a dose of about 1.76 mg to about 2 mg of huperzine, once every about 12 hours for at least two days and up to two weeks; and
i. administering a dose of about 2.1 mg to about 2.5 mg of huperzine, once every about 12 hours for at least two days;

wherein the huperzine of a.-i. is administered in a modified release pharmaceutical composition. In further embodiments the modified release pharmaceutical composition is a pharmaceutical composition according to any embodiment described herein. In further embodiments each dose prior to the maintenance dose is administered for 2 days to two weeks.

Some embodiments describe a method of treating a neurological disorder and/or a seizure disorder, in a patient in need thereof, wherein the patient experiences a better side effect profile, comprising administering a first dosing regimen of at least one dosing regimen selected from a. to h. (as further described below) and administering a second dosing regimen of at least one dosing regimen selected from a. to i. (as further described below), provided the second dosing regimen ascends from the first dosing regimen and further provided the last dosing regimen is the maintenance dose and therefore will be administered for as long as the patient is in need of treatment thereof:
a. administering a dose of about 0.25 mg of huperzine, once every about 12 hours for at least two days and up to two weeks;
b. administering a dose of about 0.5 mg of huperzine, once every about 12 hours for at least two days and up to two weeks;
c. administering a dose of about 0.75 mg of huperzine, once every about 12 hours for at least two days and up to two weeks;
d. administering a dose of about 1 mg of huperzine, once every about 12 hours for at least two days and up to two weeks;
e. administering a dose of about 1.25 mg of huperzine, once every about 12 hours for at least two days and up to two weeks;
f. administering a dose of about 1.5 mg of huperzine, once every about 12 hours for at least two days and up to two weeks;
g. administering a dose of about 1.75 mg of huperzine, once every about 12 hours for at least two days and up to two weeks;
h. administering a dose of about 2 mg of huperzine, once every about 12 hours for at least two days and up to two weeks;
i. administering a dose of about 2.5 mg of huperzine, once every about 12 hours for at least two days;

wherein the huperzine of a.-i. is administered in a modified release pharmaceutical composition. In further embodiments the modified release pharmaceutical composition is a pharmaceutical composition according to any embodiment described herein. In further embodiments each dose prior to the maintenance dose is administered for 2 days to two weeks. It will be understood that any combination of at least one dosing regimen selected from a. to h. and at least one dosing regimen selected from a. to i., allows for any combination of dosing regimens and thus describes a minimum of two dosing regimens (1 initial dose lower than the maintenance dose and 1 maintenance dose) and a maximum of 9 dosing regimens (ascending dosing regimens a. through h and maintenance dose i.).

In some embodiments the method comprises administering any dosing regimen selected from the following (wherein the last designated dose is the maintenance dose):

| | | | | | |
|---|---|---|---|---|---|
| a to i; | a to h; | a to g; | a to f; | a to e; | a to d; |
| a, b, c; | a, b; | a, c to i; | a, c to h; | a, c to g; | a, c to f; |
| a, c to e; | a, c, d; | a, b, d to i; | a, b, d to h; | a, b, d to g; | a, b, d to f; |
| a, b, d, e; | a, b, d; | a to c, e to i; | a to c, e to h; | a to c, e to g; | a to c, e, f; |
| a to c, e; | a to d, f to i; | a to d, f to h; | a to d, f to g; | a to d, f; | a to e, g to i; |
| a to e, g, h; | a to e, g; | a to f, h, i; | a to f, h; | a to g, I; | b to i; |
| b to h; | b to g; | b to f; | b to e; | b to d; | b, d to i; |
| b, d to h; | b, d to g; | b, d to f; | b, d, e; | b, d; | b, c, e to i; |
| b, c, e to h; | b, c, e to g; | b, c, e, f; | b, c, e; | b, c; | b to d, f to i; |
| b to d, f to h; | b to d, f, g; | b to d, f; | b to e, g to i; | b to e, g, h; | b to e, g; |
| b to f, h, i; | b to f, h; | b to g, I; | c to i; | c to h; | c to g; |
| c to f; | c to e; | c, d; | c, e to i; | c, e to h; | c, e to g; |
| c, e, f; | c, e; | c, d, f to i; | c, d, f to h; | c, d, f, g; | c, d, f; |
| c to e, g to i; | b to e, g, h; | c to e, g; | c to f, h, i; | c to f, h; | c to g, i |

In some embodiments, the method comprises
a. administering a dose of about 0.25 mg of huperzine A, once every about 12 hours for two days to two weeks;
b. administering a dose of about 0.5 mg of huperzine A, once every about 12 hours for two days to two weeks;
c. administering a dose of about 0.75 mg of huperzine A, once every about 12 hours for two days to two weeks; and
d. administering a dose of about 1 mg of huperzine A, once every about 12 hours for at least two days.

In some embodiments step d. is administered for as long as the patient is in need of treatment.

In some embodiments, the method further comprises after step d.:
e. administering a dose of about 1.25 mg of huperzine A once every about 12 hours for as long as the patient is in need thereof.

In some embodiments, the method further comprises after step d.:

e. administering a dose of about 1.25 mg of huperzine A once every about 12 hours for 2 days to 2 weeks;

f. administering a dose of about 1.5 mg of huperzine A once every about 12 hours for 2 days to 2 weeks;

In some embodiments, the method further comprises after step d.:

e. administering a dose of about 1.25 mg of huperzine A once every about 12 hours for 2 days to 2 weeks;

f. administering a dose of about 1.5 mg of huperzine A once every about 12 hours for 2 days to 2 weeks;

g. administering a dose of about 1.75 mg of huperzine A once every about 12 hours for as long as the patient is in need thereof.

In some embodiments, the method further comprises after step d.:

e. administering a dose of about 1.25 mg of huperzine A once every about 12 hours for 2 days to 2 weeks;

f. administering a dose of about 1.5 mg of huperzine A once every about 12 hours for 2 days to 2 weeks;

g. administering a dose of about 1.75 mg of huperzine A once every about 12 hours for 2 days to 2 weeks;

h. administering a dose of about 2 mg of huperzine A once every about 12 hours for as long as the patient is in need thereof.

In some embodiments, the method further comprises after step d.:

e. administering a dose of about 1.25 mg of huperzine A once every about 12 hours for 2 days to 2 weeks;

f. administering a dose of about 1.5 mg of huperzine A once every about 12 hours for 2 days to 2 weeks;

g. administering a dose of about 1.75 mg of huperzine A once every about 12 hours for 2 days to 2 weeks;

h. administering a dose of about 2 mg of huperzine A once every about 12 hours for 2 days to 2 weeks;

i. administering a dose of about 2.5 mg of huperzine A once every about 12 hours for as long as the patient is in need thereof.

Some embodiments of the present disclosure are directed to a method of treating a neurological disorder and/or a seizure disorder, in a patient in need thereof, wherein the patient experiences a better side effect profile, comprising administering a modified release pharmaceutical composition of huperzine, wherein the modified release pharmaceutical composition of huperzine is characterized by a $C_{ss}$ of huperzine in plasma selected from

| Dose (mg) | Css (ng/mL) |
|---|---|
| 0.25 | about 0.52 to about 0.82 |
| 0.50 | about 1.91 to about 2.99 |
| 0.75 | about 3.56 to about 5.55 |
| 1.0 | about 5.58 to about 8.72 |
| 1.25 | about 8.22 to about 12.84 |
| 1.50 | about 9.02 to about 14.09 |
| 1.75 | about 10.04 to about 15.69 |
| 2.0 | about 16 to about 25 |
| 2.5 | about 18.48 to about 28.88 |

In some embodiments the Css of huperzine in plasma is selected from

| Dose (mg) | Css (ng/mL) |
|---|---|
| 0.25 | 0.59 to about 0.72 |
| 0.50 | 2.15 to about 2.63 |
| 0.75 | 4.0 to about 4.89 |
| 1.0 | 6.28 to about 7.68 |
| 1.25 | 9.24 to about 11.30 |
| 1.50 | 10.14 to about 12.4 |
| 1.75 | 11.3 to about 13.8 |
| 2.0 | 18 to about 22 |
| 2.5 | 20.79 to about 25.41 |

In some embodiments the Css of huperzine in plasma is selected from

| Dose (mg) | Css (ng/mL) |
|---|---|
| 0.25 | about 0.652 |
| 0.50 | about 2.391 |
| 0.75 | about 4.445 |
| 1.0 | about 6.978 |
| 1.25 | about 10.27 |
| 1.50 | about 11.27 |
| 1.75 | about 12.55 |
| 2.0 | about 20 |
| 2.5 | about 23.1 |

In further embodiments the modified release pharmaceutical composition is a pharmaceutical composition according to any embodiment described herein.

Some embodiments describe a method of treating a neurological disorder and/or seizure disorder, to a patient in need thereof, wherein the patient experiences a better side effect profile, comprising administering a modified release pharmaceutical composition of huperzine A, wherein the modified release pharmaceutical composition of huperzine is characterized by a Css of huperzine in plasma of about 0.6 ng/mL to about 12 ng/mL when administered at a therapeutically effective dose. In some embodiments the Css of huperzine in plasma is about 2 ng/mL to about 12 ng/mL when administered at a therapeutically effective dose. In some embodiments the Css of huperzine in plasma is about 4 ng/mL to about 12 ng/mL when administered at a therapeutically effective dose. In some embodiments the Css of huperzine in plasma is about 6 ng/mL to about 12 ng/mL when administered at a therapeutically effective dose. In some embodiments the Css of huperzine in plasma is about 4 ng/mL to about 10 ng/mL when administered at a therapeutically effective dose. In some embodiments the Css of huperzine in plasma is about 4 ng/mL to about 8 ng/mL when administered at a therapeutically effective dose. In some embodiments the Css of huperzine in plasma is about 6.4 ng/mL to about 10 ng/mL when administered at a therapeutically effective dose. In some embodiments the Css of huperzine in plasma is about 8 ng/mL when administered at a therapeutically effective dose. In some embodiments the Css of huperzine in plasma is at least 8 ng/mL when administered at a therapeutically effective dose. In further embodiments the modified release pharmaceutical composition is a pharmaceutical composition according to any embodiment described herein.

Some embodiments of the present disclosure are directed to a method of treating a neurological or seizure disorder comprising administering to a patient in need thereof, a modified release pharmaceutical composition of huperzine, wherein the pharmaceutical composition has a pharmacokinetic profile as defined in Table 4 upon oral administration of a therapeutically effective dose of the pharmaceutical composition to a human subject. In some embodiments the modified release pharmaceutical composition of huperzine is a pharmaceutical composition according to any embodiment described herein. In some embodiments the modified huperzine pharmaceutical composition is pharmaceutical composition 4D.

TABLE 4

| Dose | $C_{max}$ ng/ml | $T_{max}$ (h) | $AUC_{0-8}$ µg · h/L |
| --- | --- | --- | --- |
| 0.25 mg | about 0.76 to about 1.19 | about 4 to about 6.25 | about 4.18 to about 6.53 |
| 0.5 mg | about 2.51 to about 3.93 | about 4 to about 6.25 | about 13.76 to about 21.5 |

In some embodiments the pharmacokinetic profile is as defined in Table 5 upon oral administration of a therapeutically effective dose of the pharmaceutical composition to a human subject.

TABLE 5

| Dose | $C_{max}$ ng/ml | $T_{max}$ (h) | $AUC_{0-8}$ µg · h/L |
| --- | --- | --- | --- |
| 0.25 mg | about 0.86 to about 1.05 | about 4.5 to about 5.5 | about 4.7 to about 5.74 |
| 0.5 mg | about 2.83 to about 3.46 | about 4.5 to about 5.5 | about 15.48 to about 18.9 |

In some embodiments the pharmacokinetic profile is as defined in Table 6 upon oral administration of a therapeutically effective dose of the pharmaceutical composition to a human subject.

TABLE 6

| Dose | $C_{max}$ ng/ml | $T_{max}$ (h) | $AUC_{0-8}$ µg · h/L |
| --- | --- | --- | --- |
| 0.25 mg | about 0.95 | about 5 | about 5.22 |
| 0.5 mg | about 3.14 | about 5 | about 17.2 |

Some embodiments of the present disclosure are directed to a method of treating a neurological or seizure disorder comprising administering to a patient in need thereof, a modified release pharmaceutical composition of huperzine, wherein the pharmaceutical composition has a pharmacokinetic profile as defined in Table 7 upon oral administration of a therapeutically effective dose of the pharmaceutical composition to a human subject. In some embodiments the modified release pharmaceutical composition of huperzine is a pharmaceutical composition according to any embodiment described herein. In some embodiments the modified huperzine pharmaceutical composition is pharmaceutical composition 4E.

TABLE 7

| Dose | $C_{max}$ ng/ml | $T_{max}$ (h) | $AUC_{0-8}$ µg · h/L |
| --- | --- | --- | --- |
| 0.5 mg | about 1.90 to about 2.96 | about 4.8 to about 7.5 | about 12.12 to about 18.94 |

In some embodiments the pharmacokinetic profile is as defined in Table 8 upon oral administration of a therapeutically effective dose of the pharmaceutical composition to a human subject.

TABLE 8

| Dose | $C_{max}$ ng/ml | $T_{max}$ (h) | $AUC_{0-8}$ µg · h/L |
| --- | --- | --- | --- |
| 0.5 mg | about 2.13 to about 2.61 | about 5.4 to about 6.6 | about 13.64 to about 16.67 |

In some embodiments the pharmacokinetic profile is as defined in Table 9 upon oral administration of a therapeutically effective dose of the pharmaceutical composition to a human subject.

TABLE 9

| Dose | $C_{max}$ ng/ml | $T_{max}$ (h) | $AUC_{0-8}$ µg · h/L |
| --- | --- | --- | --- |
| 0.5 mg | about 2.37 | about 6 | about 15.15 |

Some embodiments of the present disclosure are directed to a method of treating a neurological and/or seizure disorder comprising administering to a patient in need thereof, a modified release pharmaceutical composition of huperzine, wherein the pharmaceutical composition has a pharmacokinetic profile as defined in Table 10 upon oral administration of a therapeutically effective dose of the pharmaceutical composition to a human subject. In some embodiments the modified release pharmaceutical composition of huperzine is a pharmaceutical composition according to any embodiment described herein. In some embodiments the modified huperzine pharmaceutical composition is pharmaceutical composition 4D.

TABLE 10

| Dose of huperzine | Time (h) | Plasma concentration ng/ml |
| --- | --- | --- |
| 0.25 mg | 0.5 | about 0.17 to about 0.26 |
| | 2 | about 0.30 to about 0.48 |
| | 4 | about 0.76 to about 1.19 |
| | 6 | about 0.66 to about 1.0 |
| | 8 | about 0.6 to about 0.94 |
| 0.5 mg | 0 | about 0.62 to about 0.96 |
| | 0.5 | about 0.68 to about 1.05 |
| | 2 | about 1.68 to about 2.63 |
| | 4 | about 2.38 to about 3.71 |
| | 6 | about 2.51 to about 3.93 |
| | 8 | about 1.76 to about 2.75 |
| 0.75 mg | 0 | about 1.78 to about 2.78 |
| | 0.5 | about 1.96 to about 3.06 |
| | 2 | about 3.54 to about 5.54 |
| | 4 | about 4.4 to about 6.88 |
| | 6 | about 3.76 to about 5.88 |
| | 8 | about 3.53 to about 5.51 |
| 1.0 mg | 0 | about 3.28 to about 5.13 |
| | 0.5 | about 3.34 to about 5.21 |
| | 2 | about 6.2 to about 9.7 |
| | 4 | about 6.06 to about 9.48 |
| | 6 | about 6.41 to about 10.01 |
| | 8 | about 5.13 to about 8.01 |
| 1.25 mg | 0 | about 4.6 to about 7.19 |
| | 0.5 | about 4.52 to about 7.06 |
| | 2 | about 5.88 to about 9.19 |
| | 4 | about 10.03 to about 15.68 |
| | 6 | about 10.85 to about 16.95 |
| | 8 | about 8.37 to about 13.08 |
| 1.5 mg | 0 | About 6.17 to about 9.64 |
| | 0.5 | about 5.70 to about 8.91 |
| | 2 | about 8.4 to about 13.13 |
| | 4 | about 10.65 to about 16.62 |
| | 6 | about 10 to about 15.63 |
| | 8 | about 8.88 to about 13.88 |

TABLE 10-continued

| Dose of huperzine | Time (h) | Plasma concentration ng/ml |
|---|---|---|
| 1.75 mg | 0 | about 7.77 to about 12.14 |
|  | 0.5 | about 6.78 to about 10.6 |
|  | 2 | about 8.37 to about 13.08 |
|  | 4 | about 11.92 to about 18.63 |
|  | 6 | about 10.89 to about 17.01 |
|  | 8 | about 11.1 to about 17.34 |
| 2.0 mg | 0 | about 9.84 to about 15.38 |
|  | 0.5 | about 10.88 to about 17 |
|  | 2 | about 15.44 to about 24.13 |
|  | 4 | about 18.72 to about 29.25 |
|  | 6 | about 16.96 to about 26.5 |
|  | 8 | about 16.08 to about 25.13 |
| 2.5 mg | 0 | about 13.6 to about 21.25 |
|  | 0.5 | about 16.08 to about 25.13 |
|  | 2 | about 17.68 to about 27.63 |
|  | 4 | about 21.36 to about 33.37 |
|  | 6 | about 19.84 to about 31 |
|  | 8 | about 14.89 to about 23.25 |

In some embodiments the pharmacokinetic profile is as defined in Table 11 upon oral administration of a therapeutically effective dose of the pharmaceutical composition to a human subject.

TABLE 11

| Dose of huperzine | Time (h) | Plasma concentration ng/ml |
|---|---|---|
| 0.25 mg | 0.5 | about 0.19 to about 0.23 |
|  | 2 | about 0.34 to about 0.42 |
|  | 4 | about 0.86 to about 1.05 |
|  | 6 | about 0.74 to about 0.90 |
|  | 8 | about 0.68 to about 0.83 |
| 0.5 mg | 0 | about 0.69 to about 0.85 |
|  | 0.5 | about 0.77 to about 0.94 |
|  | 2 | about 1.89 to about 2.31 |
|  | 4 | about 2.67 to about 3.27 |
|  | 6 | about 2.83 to about 3.45 |
|  | 8 | about 1.98 to about 2.42 |
| 0.75 mg | 0 | about 2 to about 2.45 |
|  | 0.5 | about 2.21 to about 2.70 |
|  | 2 | about 3.99 to about 4.87 |
|  | 4 | about 4.95 to about 6.05 |
|  | 6 | about 4.23 to about 5.17 |
|  | 8 | about 3.97 to about 4.85 |
| 1.0 mg | 0 | about 3.69 to about 4.51 |
|  | 0.5 | about 3.75 to about 4.59 |
|  | 2 | about 6.98 to about 8.54 |
|  | 4 | about 6.82 to about 8.34 |
|  | 6 | about 7.21 to about 8.81 |
|  | 8 | about 5.77 to about 7.05 |
| 1.25 mg | 0 | about 5.18 to about 6.33 |
|  | 0.5 | about 5.09 to about 6.22 |
|  | 2 | about 6.62 to about 8.09 |
|  | 4 | about 11.29 to about 13.79 |
|  | 6 | about 12.20 to about 14.92 |
|  | 8 | about 9.41 to about 11.51 |
| 1.5 mg | 0 | about 6.94 to about 8.48 |
|  | 0.5 | about 6.42 to about 7.84 |
|  | 2 | about 9.45 to about 11.55 |
|  | 4 | about 11.97 to about 14.63 |
|  | 6 | about 11.25 to about 13.75 |
|  | 8 | about 9.99 to about 12.21 |
| 1.75 mg | 0 | about 8.74 to about 10.68 |
|  | 0.5 | about 7.63 to about 9.33 |
|  | 2 | About 9.41 to about 11.51 |
|  | 4 | about 13.41 to about 16.39 |
|  | 6 | about 12.25 to about 14.97 |
|  | 8 | about 12.48 to about 15.26 |
| 2.0 mg | 0 | about 11.07 to about 13.53 |
|  | 0.5 | about 12.24 to about 14.96 |
|  | 2 | about 17.37 to about 21.23 |
|  | 4 | about 21.06 to about 25.74 |
|  | 6 | about 19.08 to about 23.32 |
|  | 8 | about 18.09 to about 22.11 |

TABLE 11-continued

| Dose of huperzine | Time (h) | Plasma concentration ng/ml |
|---|---|---|
| 2.5 mg | 0 | about 15.3 to about 18.7 |
|  | 0.5 | about 18.09 to about 22.11 |
|  | 2 | about 19.89 to about 24.31 |
|  | 4 | about 24.03 to about 29.37 |
|  | 6 | about 22.32 to about 27.28 |
|  | 8 | about 16.74 to about 20.46 |

In some embodiments the pharmacokinetic profile is as defined in Table 12 upon oral administration of a therapeutically effective dose of the pharmaceutical composition to a human subject.

TABLE 12

| Dose of huperzine | Time (h) | Plasma concentration ng/ml |
|---|---|---|
| 0.25 mg | 0.5 | about 0.21 |
|  | 2 | about 0.38 |
|  | 4 | about 0.95 |
|  | 6 | about 0.82 |
|  | 8 | about 0.75 |
| 0.5 mg | 0 | about 0.77 |
|  | 0.5 | about 0.85 |
|  | 2 | about 2.10 |
|  | 4 | about 2.97 |
|  | 6 | about 3.14 |
|  | 8 | about 2.20 |
| 0.75 mg | 0 | about 2.22 |
|  | 0.5 | about 2.45 |
|  | 2 | about 4.43 |
|  | 4 | about 5.5 |
|  | 6 | about 4.70 |
|  | 8 | about 4.41 |
| 1.0 mg | 0 | about 4.1 |
|  | 0.5 | about 4.17 |
|  | 2 | about 7.76 |
|  | 4 | about 7.58 |
|  | 6 | about 8.01 |
|  | 8 | about 6.41 |
| 1.25 mg | 0 | about 5.75 |
|  | 0.5 | about 5.65 |
|  | 2 | about 7.35 |
|  | 4 | about 12.54 |
|  | 6 | about 13.56 |
|  | 8 | about 10.46 |
| 1.5 mg | 0 | about 7.71 |
|  | 0.5 | about 7.13 |
|  | 2 | about 10.5 |
|  | 4 | about 13.3 |
|  | 6 | about 12.5 |
|  | 8 | about 11.1 |
| 1.75 mg | 0 | about 9.71 |
|  | 0.5 | about 8.48 |
|  | 2 | about 10.46 |
|  | 4 | about 14.9 |
|  | 6 | about 13.61 |
|  | 8 | about 13.87 |
| 2.0 mg | 0 | about 12.3 |
|  | 0.5 | about 13.6 |
|  | 2 | about 19.3 |
|  | 4 | about 23.4 |
|  | 6 | about 21.2 |
|  | 8 | about 20.1 |
| 2.5 mg | 0 | about 17.0 |
|  | 0.5 | about 20.1 |
|  | 2 | about 22.1 |
|  | 4 | about 26.7 |
|  | 6 | about 24.8 |
|  | 8 | about 18.6 |

Some embodiments of the present disclosure are directed to a method of treating a neurological and/or seizure disorder comprising administering to a patient in need thereof, a modified release pharmaceutical composition of huperzine, wherein the pharmaceutical composition has a pharmacokinetic profile as defined in Table 13 upon oral administration of a therapeutically effective dose of the pharmaceutical composition to a human subject. In some embodiments the modified release pharmaceutical composition of huperzine is a pharmaceutical composition according to any embodiment described herein. In some embodiments the modified huperzine pharmaceutical composition is pharmaceutical composition 4E.

TABLE 13

| Dose of huperzine | Time (h) | Plasma concentration ng/ml |
|---|---|---|
| 0.5 mg | 0.5 | about 0.78 to about 1.23 |
| | 2 | about 1.24 to about 1.94 |
| | 4 | about 1.81 to about 2.83 |
| | 6 | about 1.90 to about 2.96 |
| | 8 | about 1.66 to about 2.59 |
| 1.0 mg | 0.5 | about 2.96 to about 4.63 |
| | 2 | about 4.52 to about 7.06 |
| | 4 | about 6.44 to about 10.06 |
| | 6 | about 5 to about 7.81 |
| | 8 | about 3.95 to about 6.18 |

In some embodiments the pharmacokinetic profile is as defined in Table 14 upon oral administration of a therapeutically effective dose of the pharmaceutical composition to a human subject.

TABLE 14

| Dose of huperzine | Time (h) | Plasma concentration ng/ml |
|---|---|---|
| 0.5 mg | 0.5 | about 0.88 to about 1.08 |
| | 2 | about 1.39 to about 1.71 |
| | 4 | about 2.03 to about 2.49 |
| | 6 | about 2.13 to about 2.61 |
| | 8 | about 1.86 to about 2.28 |
| 1.0 mg | 0.5 | about 3.33 to about 4.07 |
| | 2 | about 5.09 to about 6.22 |
| | 4 | about 7.25 to about 8.86 |
| | 6 | about 5.63 to about 6.88 |
| | 8 | about 4.45 to about 5.43 |

In some embodiments the pharmacokinetic profile is as defined in Table 15 upon oral administration of a therapeutically effective dose of the pharmaceutical composition to a human subject.

TABLE 15

| Dose of huperzine | Time (h) | Plasma concentration ng/ml |
|---|---|---|
| 0.5 mg | 0.5 | about 0.98 |
| | 2 | about 1.55 |
| | 4 | about 2.26 |
| | 6 | about 2.37 |
| | 8 | about 2.07 |
| 1.0 mg | 0.5 | about 3.70 |
| | 2 | about 5.65 |
| | 4 | about 8.05 |
| | 6 | about 6.25 |
| | 8 | about 4.94 |

Some embodiments of the present disclosure are directed to a method of treating a neurological or seizure disorder comprising administering to a patient in need thereof, a modified release pharmaceutical composition of huperzine, wherein the pharmaceutical composition has a pharmacokinetic profile as defined in Table 16 upon oral administration of a therapeutically effective dose of the pharmaceutical composition to a human subject. In some embodiments the modified release pharmaceutical composition of huperzine is a pharmaceutical composition according to any embodiment described herein. In some embodiments the modified huperzine pharmaceutical composition is pharmaceutical composition 4F-1.

TABLE 16

| Dose (mg) | Plasma concentration (ng/mL) |
|---|---|
| 0.25 | about 1.36 to about 2.13 |
| 0.50 | about 2.02 to about 3.15 |
| 0.75 | about 4.45 to about 6.95 |
| 1.25 | about 3.82 to about 5.96 |

Some embodiments of the present disclosure are directed to a method of treating a neurological or seizure disorder comprising administering to a patient in need thereof, a modified release pharmaceutical composition of huperzine, wherein the pharmaceutical composition has a pharmacokinetic profile as defined in Table 17 upon oral administration of a therapeutically effective dose of the pharmaceutical composition to a human subject. In some embodiments the modified release pharmaceutical composition of huperzine is a pharmaceutical composition according to any embodiment described herein. In some embodiments the modified huperzine pharmaceutical composition is pharmaceutical composition 4F-1.

TABLE 17

| Dose (mg) | Plasma concentration (ng/mL) |
|---|---|
| 0.25 | about 1.53 to about 1.87 |
| 0.50 | about 2.27 to about 2.77 |
| 0.75 | about 5.00 to about 6.12 |
| 1.25 | about 4.29 to about 5.25 |

Some embodiments of the present disclosure are directed to a method of treating a neurological and/or seizure disorder comprising administering to a patient in need thereof, a modified release pharmaceutical composition of huperzine, wherein the pharmaceutical composition has a pharmacokinetic profile as defined in Table 18 upon oral administration of a therapeutically effective dose of the pharmaceutical composition to a human subject. In some embodiments the modified release pharmaceutical composition of huperzine is a pharmaceutical composition according to any embodiment described herein. In some embodiments the modified huperzine pharmaceutical composition is pharmaceutical composition 4F-1.

TABLE 18

| Dose (mg) | Plasma concentration (ng/mL) |
|---|---|
| 0.25 | about 1.7 |
| 0.50 | about 2.52 |
| 0.75 | about 5.56 |
| 1.25 | about 4.77 |

The pharmaceutical compositions of the present invention can be administered in a combination with other therapeutic agent(s). The choice of therapeutic agents that can be co-administered with the composition of the invention will depend, in part, on the condition being treated. For example, the compounds of the invention can be administered in combination with other agents, such as acetaminophen, acetazolamide, alprazolam, armodafinil, benzodiazepines, brivaracetam, busprirone, cannabinoids, carbamazepine, carisoprodol, chlordiazepoxide, chloroxazone, clobazam, clonazepam, clorazepate, cyclobenzaprine, diazepam, divalproex, erenumab-aooe, eslicarbazine, ethosuximide, ezogabine, felbamate, flunarizine, fosphenytoin, gabapentin, hydroxyzine, ibuprofen, lacosamide, lamotrigine, levetiracetam, lorazepam, metaxalone, methocarbamolimipramine, methsuximide, modafinil, naproxen, nitrazepam, oxcarbazepine, perampanel, phenobarbital, phenytoin, pregabalin, primidone, propranolol, rufinamide, stiripental, tiagabine, topiramate, valproic acid, vigabatrin, and zonisamide or combinations thereof, used to treat other symptoms and side effects commonly associated with epilepsy or seizures, such as fainting, fatigue, muscle spasms, auras, amnesia, anxiety, depression, headaches, sleepiness, or staring spells.

Such other therapeutic agent(s) may be administered prior to, simultaneously with or following the administration of huperzine pharmaceutical composition according to any embodiment described herein.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various embodiments of the present invention will be illustrated with reference to the following non-limiting examples. The following examples are for illustrative purposes only and are not to be construed as limiting the invention in any manner.

Example 1: In Vitro Dissolution Testing

The compositions were tested according to USP 1 type apparatus at 50 revolutions per minute in 50 mM phosphate (pH 6.8) at 37° C. Results are shown in FIG. 4.

Example 2: Pharmacokinetic Study in Dogs

A Study Objective

The objective of this study was to determine the plasma pharmacokinetics of modified release huperzine Composition 4A in male beagle dogs. The huperzine A was monitored in plasma for up to 24 hours.

Vehicle and Pharmaceutical Composition Preparation

Animals were dosed at a nominal dose of 5.45 mg/kg modified release huperzine A (composition 4A, equivalent to 0.049 mg/kg huperzine A)

Animal Specifications

Three, non-naïve, male, beagle dogs (Marshall Bioresources, Beijing, China) weighing≥6 kg were used in the study. Animals underwent a physical examination for general health by a staff veterinarian prior to assignment to the study. The animals were acclimated to the testing facility prior to the study.

Environmental Conditions

Animals were housed in room(s) that were controlled and monitored for relative humidity (targeted mean range 40% to 70%) and temperature (targeted mean range 18° to 26° C.) with 10 to 20 air changes/hour. The room(s) were on a 12-hour light/dark cycle except when interruptions were necessitated by study activities.

Housing

Animals were individually housed in stainless-steel mesh cages during in-life that were in accordance with the National Research Council "Guide for the Care and Use of Laboratory Animals."

Diet and Feeding

Animals were fed twice daily. The dogs were fed approximately 220 grams of Certified Dog Diet daily (Beijing Vital Keao Feed Co., Ltd. Beijing, P. R. China). These amounts could be adjusted as necessary based on food consumption of the group or an individual body weight changes of the group or an individual and/or changes in the certified diet.

Drinking Water

RO (reverses osmosis) water was made available to all animals, ad libitum.

Environmental Enrichment

Enrichment toys were provided.

Administration of Dose Pharmaceutical Composition

The modified release huperzine A composition 4A was administered orally via capsule delivery.

Dose Administration:

a. The technician pulled the lower jaw down with his/her other hand and placed the capsule far back in the throat. The capsule was then pushed past the pharynx by using a thumb or index finger. b. The capsule could be moistened with water to facilitate dosing, and water could be used to facilitate swallowing of capsules, if necessary. c. After administering the dose, swallowing could be induced, if needed, by gently stroking the dog's throat or tapping the dog under the chin. d. Immediately following capsule administration, water was given to the mouth of the animals at the dose volume of about 10 mL/animal to help capsule swallowing. e. After administration, the animal's mouth was inspected to ensure that the dose has been swallowed.

Observations and Examinations

Twice daily, cage-side observations for general health and appearance were done.

On dosing day, the animals were observed before and after each sample collection time point. General condition, behavior, activity, excretion, respiration or other unusual observations noted throughout the study were recorded in the raw data.

Body Weight

All animals were weighed on the dosing day prior to dosing to determine the dose volume to be administered.

Data analysis and Reporting

Plasma concentration versus time data was analyzed by non-compartmental approaches using the WinNonlin software program (version 6.3, Pharsight, Mountain View, CA). $C_{max}$, $T_{max}$, Clearance, $T_{1/2}$, $AUC_{0-t}$, $AUC_{0-inf}$, $MRT_{0-t}$, $MRT_{0-inf}$ and graphs of plasma concentration versus time profile were reported for each analyte. The results of the study are summarized in FIG. 5.

Example 3: Evaluation of the Bioavailability, Safety and Tolerability of Modified Release Huperzine A Following Multiple Dose Administrations in Healthy Subjects A single center, on-site/outpatient, dose escalation study was conducted with oral pharmaceutical composition 4D. The subjects were dosed twice daily (BID) in 4 cohorts of 2 subjects each (Pharmaceutical composition 4D) and 2 cohorts of 3 subjects total (Pharmaceutical composition 4E)

to assess plasma levels, safety, and allow necessary dosing alterations to occur prior to dosing any subsequent subjects. The study was conducted in an on-site setting at dose initiation and at times of dose escalation to evaluate safety, and for specimen collection for routine laboratory and pharmacokinetic analysis. Subjects were discharged and compliance of BID dosing was monitored via twice daily phone calls by site staff. The initial dose was 0.5 mg BID with a dose escalation every 2-3 days until a maximum tolerated dose was observed or a maximum of 2.5 mg BID dose was obtained. Initial dose and rate of escalation was able to be altered at the discretion of the site staff to ensure safety of the subjects.

Study Endpoints: Plasma concentration data was used for bioavailability assessment. The derived pharmacokinetic parameters include: area under the curve (AUC), maximum serum concentration ($C_{max}$), and time of $C_{max}$ ($T_{max}$).

The safety and tolerability parameters were assessed based on the occurrence of adverse events as well as the results of study-specified vital signs, neurological and physical examinations, ECG evaluations, and clinical laboratory studies.

Dosing schedule was as follows:
Cohorts 1 & 2 (Pharmaceutical composition 4D):

| Days 1, 2 | Days 3, 4 | Days 5, 6, 7 | Days 8, 9 | Days 10, 11 |
|---|---|---|---|---|
| 0.5 mg BID | 1 mg BID | 1.5 mg BID | 2.0 mg BID | 2.5 mg BID |

Cohort 3 (Pharmaceutical composition 4D):

| Days 1, 2 | Days 3, 4 | Days 5, 6, 7 | Days 8, 9 | Days 10, 11 | Days 12, 13, 14 |
|---|---|---|---|---|---|
| 0.25 mg BID | 0.5 mg BID | 1 mg BID | 1.5 mg BID | 2 mg BID | 2.5 mg BID |

Cohort 4 (Pharmaceutical composition 4D):

| Days 1, 2 | Days 3, 4 | Days 5, 6, 7 | Days 8, 9 | Days 10, 11 | Days 12, 13, 14 | Days 15, 16 | Day 17, 18 |
|---|---|---|---|---|---|---|---|
| 0.25 mg BID | 0.5 mg BID | 0.75 mg BID | 1 mg BID | 1.25 mg BID | 1.5 mg BID | 1.75 mg BID | 2.0 mg BID |

Cohort 5 and 6 (Pharmaceutical composition 4E):

| Days 1, 2 | Days 3, 4 | Days 5, 6, 7 | Days 8, 9 | Days 10, 11 | Days 12, 13, 14 | Days 15, 16 | Day 17, 18 |
|---|---|---|---|---|---|---|---|
| 0.25 mg BID | 0.5 mg BID | 0.75 mg BID | 1 mg BID | 1.25 mg BID | 1.5 mg BID | 1.75 mg BID | 2.0 mg BID |

Figure 7:
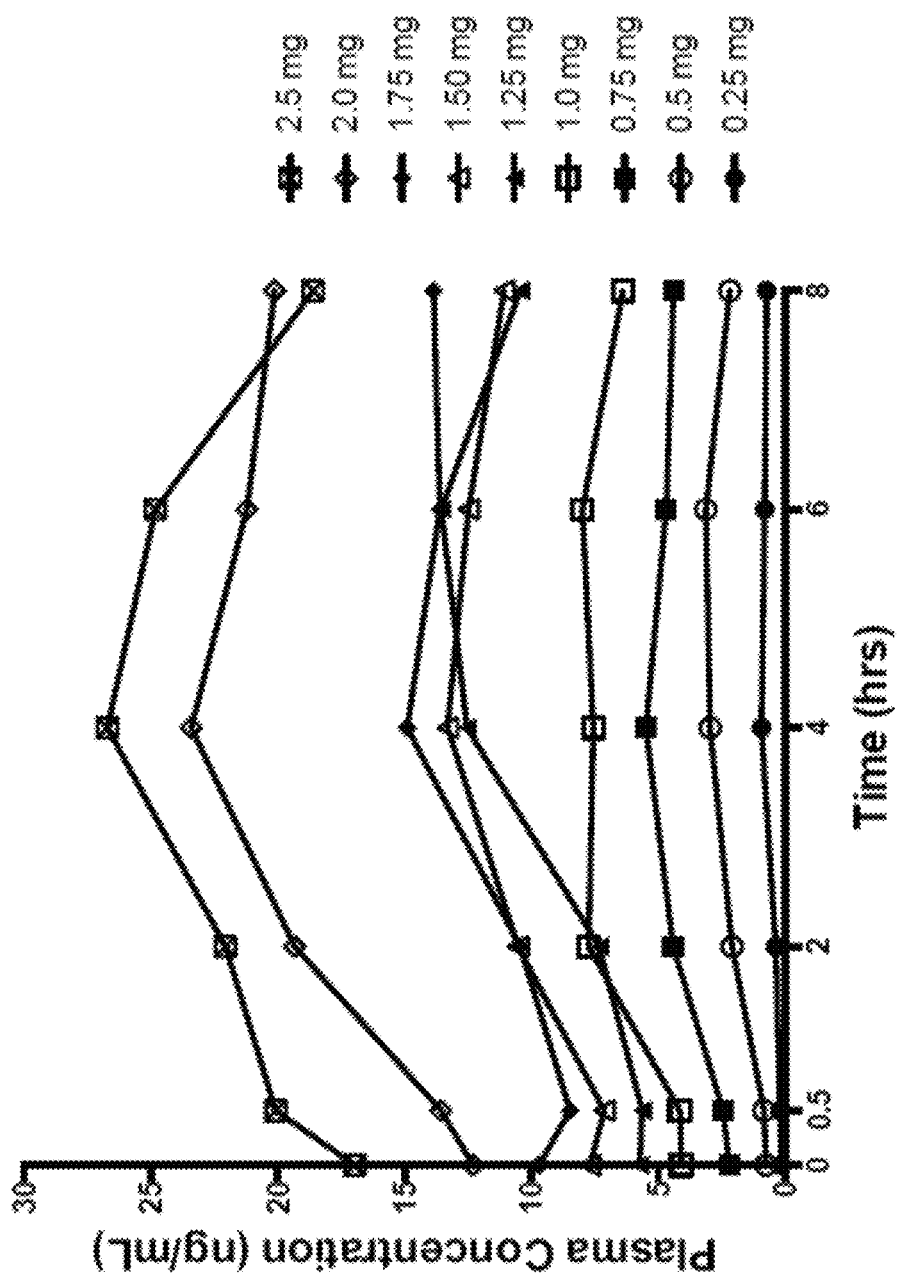
FIG. 7 shows in vivo plasma concentration in humans over time taken during dose titration of 0.25 mg (solid small circle), 0.5 mg (large circle), 0.75 mg (solid large square), 1 mg (large square), 1.25 mg (small solid triangle), 1.50 mg (small triangle), 1.75 mg (small solid diamond), 2.0 (small diamond) and 2.5 mg (box with X) of pharmaceutical composition 4D.

Plasma levels taken on dose titration inpatient days throughout the study for cohorts 1-4 are shown in FIG. 7. Plasma draws occurred throughout the dose titration schedule to assess total plasma concentrations. Time=0 represents pre-dose baseline on the titration day corresponding to the dosing schedule. Means reflect all data obtained for 8 subjects. The initial dosing schedule was altered for cohorts 3 and 4 to accommodate a slower titration (0.25 mg dose increments).

Figure 8:
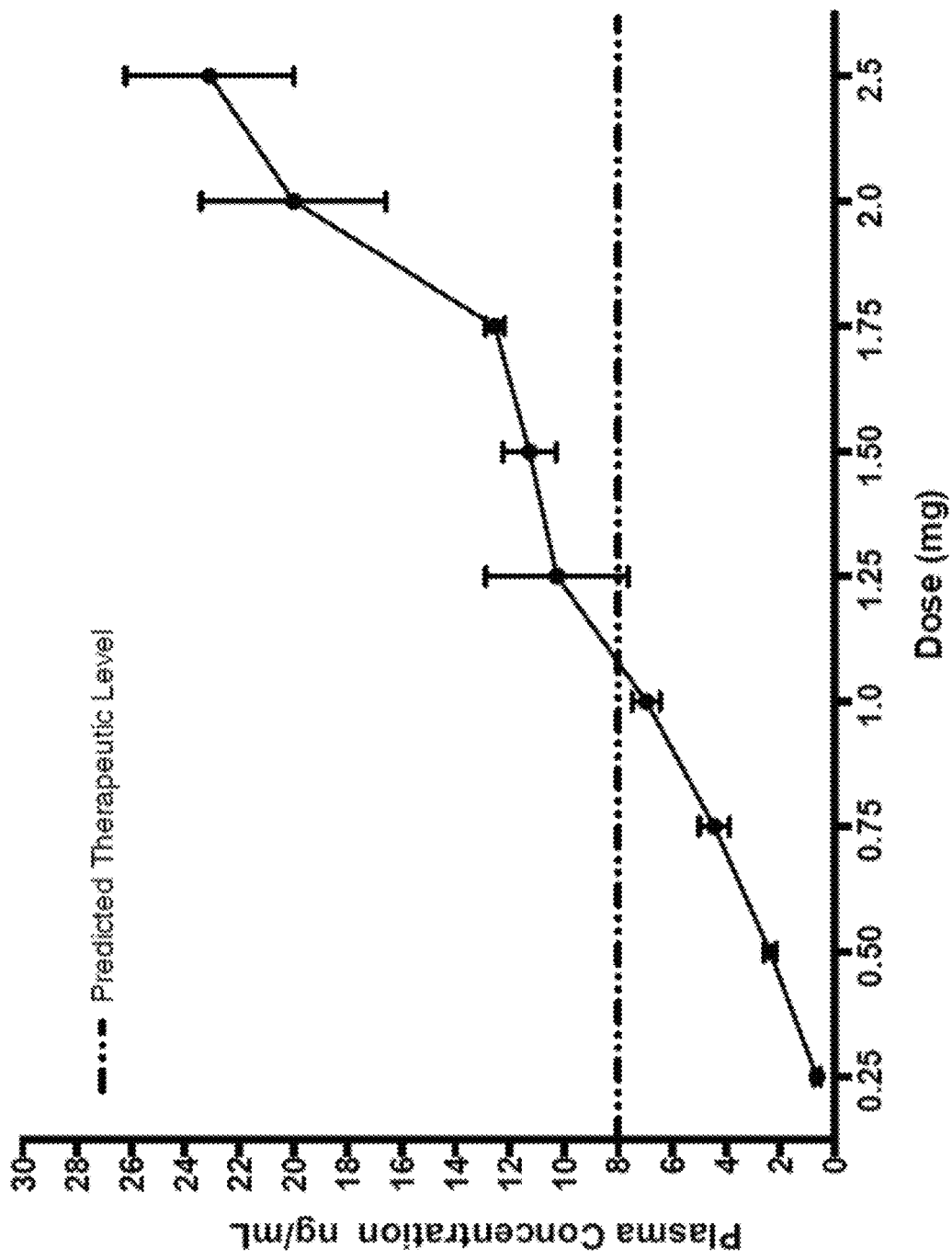
FIG. 8 is the in vivo plasma concentration ($C_{ss}$) in humans at various doses for pharmaceutical composition 4D.

A graph of the average plasma levels taken on inpatient days throughout the study at particular doses is shown in FIG. 8. Pharmacokinetic modeling predicts average plasma level (Css) of 8.4 ng/mL to achieve 100% seizure protection in 50% of patients (dosing equivalent of about 1.1-1.25 mg BID.

The compositions in the study yielded favorable pharmacokinetic profiles, demonstrated twice a day dosing and demonstrated a dramatic reduction in adverse events when compared to immediate release preparation, even with double the dose previously used. Pharmacokinetic modeling accurately predicted dose-exposure relationships for the entire dose titration.

Adverse events were mild and transient. Testing showed that approximately double the dose predicted for significant seizure control was attainable; yielding much higher, stable plasma levels of huperzine A given on a twice/day schedule, and achieved drug plasma levels predicted to provide significant seizure protection in patients with adult and childhood intractable epilepsies.

Example 4: Evaluation of Safety and Efficacy of Modified Release Pharmaceutical Compositions of Huperzine for the Treatment of Adult Focal Impaired Awareness Seizures (FIAS)

The purpose of this study is to examine safety signals and demonstrate seizure reduction in adults with FIAS treated with modified release pharmaceutical compositions of huperzine as an add-on therapy in an in-patient and out-patient study with the pharmaceutical composition according to any embodiment described herein. In some embodiments the pharmaceutical composition is 4F1 or 4F-2.

Dose administration for each participant will begin at 0.25 mg BID escalating sequentially every 4 days to a maximum tolerated dose or target dose of 1.75 mg BID Participants who are unable to tolerate a dose during dose escalation will have their dose reduced to the prior tolerable dose; if unable to tolerate lower doses, participants will be withdrawn from the study.

Planned Number of Participants:
Sixteen participants will be enrolled into and complete the study.

Study Design:
This study is a single center, multi-site, open-label, add-on study in otherwise healthy participants with frequent Focal Impaired Awareness Seizures.

Pre-qualified, eligible participants age 18 and older that have signed an informed consent will be enrolled into the study. The study will consist of a 96-hour baseline continuous VEM period, a one-month out-patient dose escalation treatment period, followed by a second 96-hour continuous VEM treatment period.

On Day 1 of the baseline period (after completion of physical and neurological exams, vital signs, electrocardiogram (ECG), blood sample for CBC and chemistry, urine sample collection for standard urinalysis including creatinine and electrolytes) daily seizure counting will begin and will be collected via VEM with standard lead placement. Participants will remain on stable anticonvulsant treatment regimen as determined by their treating physician. Upon completion of the baseline period (5 days in-patient VEM), participants who experienced at least 5 focal impaired awareness seizures will be immediately enrolled into treatment. They will begin dose escalation of modified release pharmaceutical composition of huperzine to either the target dose of 1.75 mg BID or a maximum tolerated dose. The modified release pharmaceutical composition of huperzine will be titrated over 28 days, escalating every 4 days. Upon reaching the target dose or maximum tolerated dose, participants will maintain that dose for the balance of the out-patient titration period, after which they will begin a 96-hour in-patient VEM treatment period. A daily seizure diary will be kept for the duration of the out-patient titration period where participants or caregivers will notate seizure type and time of day. Participants who are unable to attain target dose of 1.75 mg BID will be dose reduced to a prior tolerable dose. If unable to tolerate lower doses, participants may be withdrawn from the study. Participants will be dosed 2 times daily (every 12 hrs) with the modified release pharmaceutical composition of huperzine, administration occurring in the morning and evening. Participants will have the modified release pharmaceutical composition of huperzine discontinued at the final day of in-patient VEM unless they elect to participate in the open-label extension period, during which they will continue to record seizure diaries and will have safety assessments on a regular basis.

Blood samples for pharmacology will be drawn on selected out- and in-patient study days. Adverse events (AE) and use of concurrent medications will be recorded throughout the study.

All participants who receive at least one dose of modified release pharmaceutical composition of huperzine will be included in safety analyses that includes vital signs, clinical laboratory testing, physical and neurological examinations, electrocardiograms and adverse event monitoring.

Endpoint:

Primary Efficacy Variables: Reduction in average daily seizure count between baseline (pre-treatment) and evaluation (on treatment) VEM periods.

Secondary Efficacy Variables:

Percent reduction in average daily seizure count from the baseline VEM period compared to the evaluation VEM period (on treatment)

Percent reduction in average number of seizures from the baseline period (screening/retrospective diary) compared to the last week of the titration treatment period Percent of participants considered treatment responders defined as those with a ≥25%, ≥50%, ≥75% reduction in seizures from the baseline VEM period compared to the VEM treatment evaluation period Percent of reduction of average number of seizures vs. baseline/retrospective diary at 1, 3, 6, 12 months during the extension period Proportion of subjects with 100% seizure reduction Proportion of subjects requiring rescue medication at different dosages Pharmacology:

Plasma concentration data will be used determine a dose, serum level and seizure effect relationship.

Urine samples will undergo standard urinalysis, test drug elimination and presence of potential metabolites.

Figure 9:
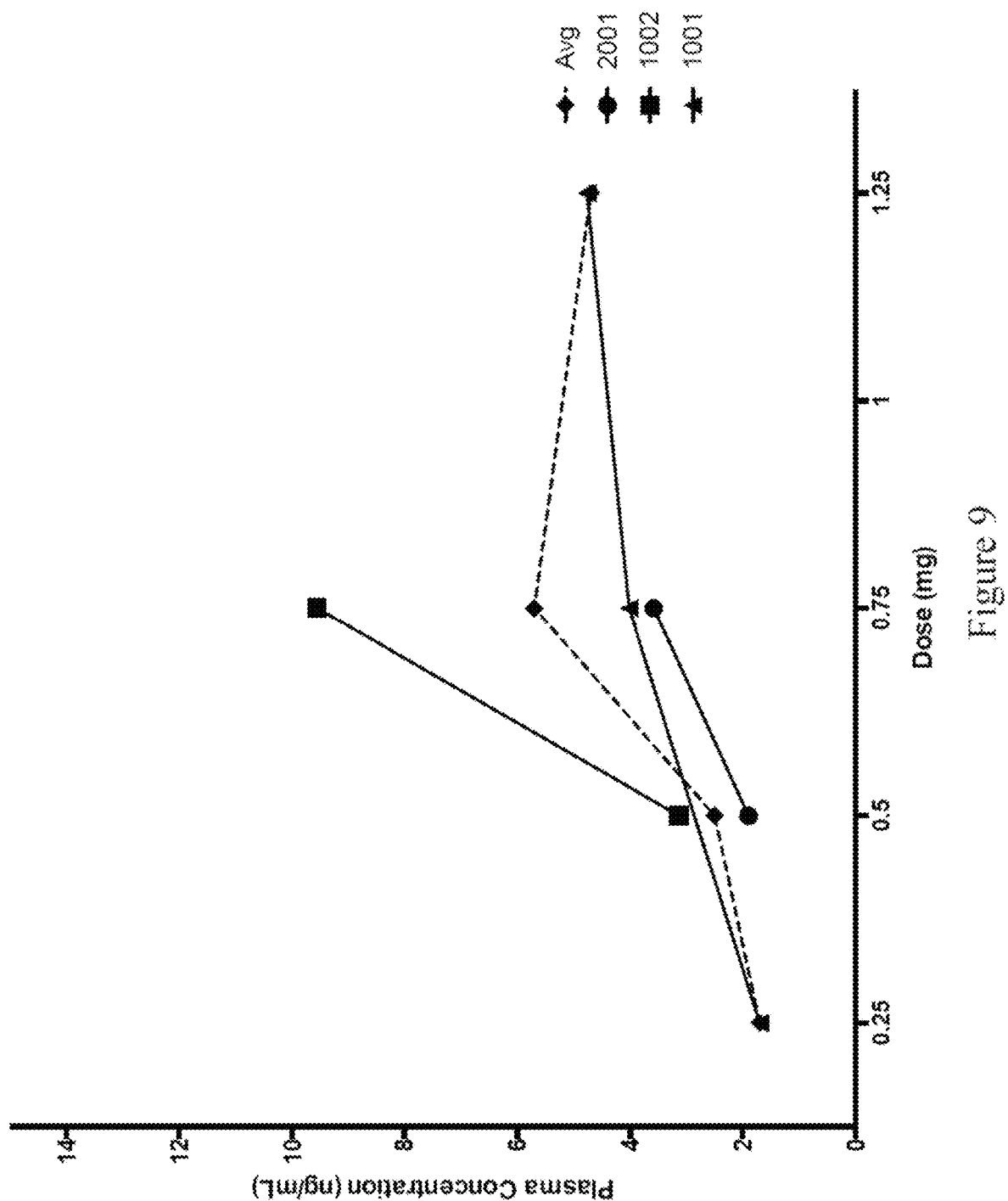
FIG. 9 shows the in vivo plasma concentration for three human patients (circle, triangle and square) and the average plasma concentration (dashed diamond line) taken during dose titration of 0.25 mg, 0.5 mg, 0.75 mg, 1.25 mg.

To date three patients have received 2-3 dose titrations as described in FIG. 9 and Table 19.

TABLE 1

| Patient | Dose (mg) | Plasma concentration (ng/mL) | Time post dose (h) |
| --- | --- | --- | --- |
| 1001 | 0.25 | 1.7 | 2.43 |
|  | 0.75 | 4.02 | 3 |
|  | 1.25 | 4.77 | 4 |
| 1002 | 0.5 | 3.13 | 5.25 |
|  | 0.75 | 9.07 | 5.25 |
| 2001 | 0.5 | 1.9 | 5.25 |
|  | 0.75 | 3.58 | 5 |

Example 5: General Procedure for the Preparation of Pharmaceutical Compositions

The pharmaceutical compositions described herein can generally be prepared as follows:

Utilizing a fluid bed coating equipment (or similar coated particle manufacturing equipment), use standard procedures and operating conditions to manufacture coated particles. These procedures include:

Prepare of solutions for manufacturing the modified release particles, e.g. solutions containing huperzine, binders, anti-caking agents, etc.

Load Uncoated Cores into Fluid Bed

Adjust all operating parameters nozzles, pressures, to appropriate ranges for the appropriate batch size and equipment being utilized Process coated pellets to remove agglomerates or fine particles outside of the desired particle size distribution.

An exemplary process comprises:
1. Solution Preparation
   a. Heat up predetermined amount of distilled water to 70 degrees centigrade.
   b. Dissolve huperzine into anhydrous ethanol by stirring.
   c. Add HPMC into the heated water with continuous stirring when needed.
   d. Add another partitioned amount of distilled water into the above solution; keep stirring until the powders are fully dissolved.
   e. Add PVP into HPMC solution and equally make it dissolve by continuous stirring.
   f. Combine HMPC/PVP solution with the huperzine ethanol solution. Flush the vessel using distilled water and carefully pour into the solution until the final weight is targeted and keep stirring for another 5 min.
2. Drug layer coating
   a. sucrose spheres of the desired size were transferred into a fluidized bed processor and the aforesaid huperzine solution of 1f. was coated onto the sucrose spheres at the product temp of 35~45 C.
3. Sustained release layer coating
   a. Plasticized ethyl cellulose solution that had been prepared ahead was coated onto the resultant huperzine loaded sugar spheres using the same product temp range above till the theoretical weight gain achieved was achieved.

The invention claimed is:

1. A method of treating a disorder selected from a neurological disorder or a seizure disorder comprising orally administering twice a day to a human patient in need thereof an oral pharmaceutical composition comprising from 0.5 mg to 2.0 mg of huperzine, said pharmaceutical composition further comprising:

a. about 74 weight % to about 86 weight % of a sugar sphere core having a particle size of about 500-710 µm;
b. a huperzine layer coating the sugar sphere, wherein the huperzine layer comprises about 0.95% to about 1 weight % huperzine or a pharmaceutically acceptable salt of huperzine that is equivalent to about 0.95% to about 1 weight % huperzine, and one or more excipients, wherein the total amount of excipients is about 5 weight % to about 9 weight %; and
c. about 7 weight % to about 16 weight % of a plasticized ethyl cellulose polymer layer coating the huperzine layer;
wherein said administering provides an in vivo steady-state concentration ($C_{ss}$) of huperzine in plasma of the human patient of at least 8 ng/mL.

2. The method of claim 1, wherein the huperzine is huperzine A or a pharmaceutically acceptable salt thereof.

3. The method of claim 1, wherein the oral pharmaceutical composition further comprises a seal coat layer coating the huperzine layer between the huperzine layer and the plasticized ethyl cellulose polymer layer.

4. The method of claim 1, wherein the one or more excipients is selected from hydroxypropyl methylcellulose, polyvinylpryrrolidone or combinations thereof.

5. The method of claim 1, wherein the one or more excipients is selected from low viscosity hydroxypropyl methylcellulose, polyvinylpryrrolidone, or combinations thereof.

6. The method of claim 1, wherein the one or more excipients is a combination of about 5 weight % to about 7 weight % hydroxypropyl methylcellulose and about 0.5 weight % to about 1.5 weight % polyvinylpryrrolidone.

7. The method of claim 1, wherein the huperzine is huperzine A and the one or more excipients is a combination of low viscosity hydroxypropyl methylcellulose and polyvinylpyrrolidone.

8. The method of claim 1, wherein the oral pharmaceutical composition comprises about 80 weight % to about 86 weight % of the sugar sphere.

9. The method of claim 1, wherein the plasticized ethyl cellulose polymer layer is about 7 weight % to about 12 weight % of the composition.

10. The method of claim 1, wherein the oral pharmaceutical composition comprises
a. about 79 weight % to about 84 weight % of the sugar sphere core;
b. a huperzine layer coating the sugar sphere, wherein the huperzine layer comprises about 0.95 weight % to about 1 weight % huperzine A, or a pharmaceutically acceptable salt of huperzine A that is equivalent to about 0.95 weight % to about 1 weight % of huperzine A; about 6 weight % hydroxypropyl methylcellulose, and about 0.95 weight % to about 1 weight % polyvinylpryrrolidone; and
c. about 8 weight % to about 13 weight % of a plasticized ethyl cellulose polymer layer coating the huperzine layer.

11. The method of claim 1, wherein the oral pharmaceutical composition comprises:
a. about 80 weight % to about 83 weight % of the sugar sphere core;
b. a huperzine layer coating the sugar sphere, wherein the huperzine layer comprises about 0.95 weight % to about 1 weight % huperzine A, about 5 weight % to about 6 weight % hydroxypropyl methylcellulose, and about 0.95 weight % to about 1 weight % polyvinylpryrrolidone; and
c. about 8 weight % to about 12 weight % of a plasticized ethyl cellulose polymer layer coating the huperzine layer.

12. The method of claim 1, wherein the oral pharmaceutical composition comprises:
a. about 81 weight % to about 82 weight % of the sugar sphere core;
b. a huperzine layer coating the sugar sphere, wherein the huperzine layer comprises about 0.95 weight % to about 1 weight % huperzine A, about 5 weight % to about 6 weight % hydroxypropyl methylcellulose, and about 0.95 weight % to about 1 weight % polyvinylpryrrolidone; and
c. about 10 weight % to about 11 weight % of a plasticized ethyl cellulose polymer layer coating the huperzine layer.

13. The method of claim 1, wherein the oral pharmaceutical composition comprises:
a. about 82 weight % to about 83 weight % the sugar sphere core;
b. a huperzine layer coating the sugar sphere, wherein the huperzine layer comprises about 0.95 weight % to about 1 weight % huperzine A, about 6 weight % hydroxypropyl methylcellulose, and about 0.95 weight % to about 1 weight % polyvinylpryrrolidone; and
c. about 9 weight % to about 10 weight % of a plasticized ethyl cellulose polymer layer coating the huperzine layer.

14. The method of claim 2, wherein the oral pharmaceutical composition comprises:
a. about 76 weight % to about 76 weight % the sugar sphere core;
b. a huperzine layer coating the sugar sphere, wherein the huperzine layer comprises about 0.9 weight % to about 1 weight % huperzine A, about 5 weight % to about 6 weight % hydroxypropyl methylcellulose, and 0.9 weight % to about 1 weight % polyvinylpryrrolidone;
c. a seal coat layer coating the huperzine layer, comprising about 1 weight % to about 2 weight % hydroxypropylmethyl cellulose; and
d. about 15 weight % to about 16 weight % of a plasticized ethyl cellulose polymer layer coating the seal coat layer.

15. The method of claim 1, wherein the oral pharmaceutical composition is in a capsule.

16. The method of claim 1, wherein the oral pharmaceutical composition comprises huperzine A, wherein said administering provides a $C_{max}$ of huperzine in plasma of the human patient of about 4 ng/ml to about 8 ng/mL, a $T_{max}$ of about 4 hours to about 8 hours and a $t_{1/2}$ of about 8 hours to about 12 hours.

17. The method of claim 16, wherein the $C_{max}$ is about 4 ng/ml to about 6 ng/mL, $T_{max}$ is about 4 hours to about 8 hours and the $t_{1/2}$ is about 10 hours to about 12 hours.

18. The method of claim 16, wherein the $C_{max}$ is about 6 ng/ml, the $T_{max}$ is about 4 hours and the $t_{1/2}$ is about 8.3 hours.

19. The method of claim 1, wherein the oral pharmaceutical composition comprising a therapeutically-effective amount of huperzine, and wherein said administering provides in the human patient a $T_{max}$ of about 4 to about 8 hours and a $C_{max}$ that is reduced by about 25% to about 50% when compared with a $C_{max}$ of an immediate release huperzine pharmaceutical composition administered at an equivalent dose.

20. The method of claim 19, wherein the $C_{max}$ provided by administering the oral pharmaceutical composition is reduced by about 50% when compared with the $C_{max}$ of the immediate release huperzine pharmaceutical composition.

21. The method of claim 1, wherein the oral pharmaceutical composition exhibits the following dissolution profile when tested according to USP 1 type apparatus at 50 revolutions per minute in 50 mM phosphate (pH 6.8) at 37° C.: about 36% to about 46% of the huperzine is released after 2 hours, about 61% to about 77% of the huperzine is released after 4 hours, about 84% to about 97% of the huperzine is released after 8 hours and not less than about 89% of the huperzine is released after 12 hours.

22. The method of claim 1, wherein the oral pharmaceutical composition exhibits the following dissolution profile when tested according to USP 1 type apparatus at 50 revolutions per minute in 50 mM phosphate (pH 6.8) at 37° C.: about 36% of the huperzine is released after 2 hours, about 63% of the huperzine is released after 4 hours, about 84% of the huperzine is released after 8 hours and not less than about 89% of the huperzine is released after 12 hours.

23. The method of claim 1, wherein the oral pharmaceutical composition exhibits the following dissolution profile when tested according to USP 1 type apparatus at 50 revolutions per minute in 50 mM phosphate (pH 6.8) at 37° C.: about 46% of the huperzine is released after 2 hours, about 77% of the huperzine is released after 4 hours, about 97% of the huperzine is released after 8 hours and not less than about 99% of the huperzine is released after 12 hours.

24. The method of claim 1, wherein the oral pharmaceutical composition exhibits the following dissolution profile when tested according to USP 1 type apparatus at 50 revolutions per minute in 50 mM phosphate (pH 6.8) at 37° C.: about 43% of the huperzine is released after 2 hours, about 68% of the huperzine is released after 4 hours, about 88% of the huperzine is released after 8 hours and not less than about 96% of the huperzine is released after 12 hours.

25. The method of claim 1, wherein the oral pharmaceutical composition exhibits the following dissolution profile when tested according to USP 1 type apparatus at 50 revolutions per minute in 50 mM phosphate (pH 6.8) at 37° C.: about 38% of the huperzine is released after 2 hours, about 61% of the huperzine is released after 4 hours, about 84% of the huperzine is released after 8 hours and not less than about 94% of the huperzine is released after 12 hours.

26. The method of claim 1, wherein the disorder is a seizure disorder selected from epilepsy and complex partial seizure.

27. The method of claim 1, wherein said administering comprises
   a. administering one or more titration doses of the pharmaceutical composition followed by
   b. administering a maintenance dose of the pharmaceutical composition wherein the maintenance dose is a therapeutically effective dose.

28. The method of claim 2, wherein said administering provides an in vivo steady-state (Css) of huperzine A in plasma of the human patient selected from the group consisting of: about 8.22 ng/ml to about 12.84 ng/ml at a 1.25 mg dose; about 9.02 ng/mL to about 14.09 ng/ml at a 1.5 mg dose; about 10.04 ng/ml to about 15.69 ng/ml at a 1.75 mg dose; and about 16 ng/mL to about 25 ng/ml at a 2.0 mg dose.

29. The method of claim 1, wherein said administering provides a $C_{max}$ of huperzine in plasma of the human patient of about 0.76 ng/mL to about 1.19 ng/ml, a $T_{max}$ of about 4 hours to about 6.25 hours and an $AUC_{0-8}$ of about 4.18 to about 6.53.

30. The method of claim 1, wherein said administering provides a $C_{max}$ of huperzine in plasma of the human patient of about 2.51 ng/mL to about 3.93 ng/ml, a $T_{max}$ of about 4 hours to about 6.25 hours and an $AUC_{0-8}$ of about 13.76 to about 21.5.

31. The method of claim 1, wherein said administering provides an in vivo plasma concentration of huperzine in the human patient between 8 ng/ml and 13 ng/ml with a dose of 1.25 mg twice-a-day (BID) of the oral pharmaceutical composition.

32. The method of claim 1, wherein said administering provides an in vivo plasma concentration of huperzine in the human patient between 17 ng/ml and 23 ng/ml with a dose of 2.0 mg BID of the oral pharmaceutical composition.

33. The method of claim 1, wherein the particle size is from about 500 μm to about 600 μm.

34. The method of claim 1, wherein huperzine is the only active ingredient of the pharmaceutical composition.

* * * * *